(12) United States Patent
Takemoto et al.

(10) Patent No.: US 8,603,111 B2
(45) Date of Patent: Dec. 10, 2013

(54) LIGATING APPARATUS

(75) Inventors: Shotaro Takemoto, Tokyo (JP); Tetsuya Yamamoto, Hanno (JP); Tatsutoshi Hashimoto, Machida (JP); Koichi Kawashima, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 717 days.

(21) Appl. No.: 11/715,542

(22) Filed: Mar. 8, 2007

(65) Prior Publication Data

US 2007/0213745 A1 Sep. 13, 2007

(30) Foreign Application Priority Data

Mar. 9, 2006 (JP) ................. P2006-064023

(51) Int. Cl.
*A61B 17/04* (2006.01)
(52) U.S. Cl.
USPC ........................................ 606/144; 606/139
(58) Field of Classification Search
USPC .......... 606/139, 148, 144, 145, 138, 140, 141
See application file for complete search history.

(56) References Cited

U.S. PATENT DOCUMENTS

| | | | | |
|---|---|---|---|---|
| 5,312,423 A | * | 5/1994 | Rosenbluth et al. .......... | 606/148 |
| 5,334,199 A | * | 8/1994 | Yoon ............................ | 606/144 |
| 5,336,229 A | | 8/1994 | Noda | |
| 5,571,120 A | * | 11/1996 | Yoon ............................ | 606/148 |
| 5,704,943 A | * | 1/1998 | Yoon et al. .................... | 606/139 |
| 5,716,368 A | * | 2/1998 | de la Torre et al. ........... | 606/148 |
| 5,810,845 A | * | 9/1998 | Yoon ............................ | 606/139 |
| 7,344,545 B2 | * | 3/2008 | Takemoto et al. ............ | 606/144 |
| 7,527,590 B2 | * | 5/2009 | Suzuki et al. ................. | 600/104 |
| 7,530,985 B2 | * | 5/2009 | Takemoto et al. ............ | 606/144 |
| 2003/0181924 A1 | * | 9/2003 | Yamamoto et al. ........... | 606/144 |
| 2003/0216613 A1 | * | 11/2003 | Suzuki et al. ................. | 600/104 |
| 2004/0147941 A1 | * | 7/2004 | Takemoto et al. ............ | 606/144 |
| 2005/0149067 A1 | * | 7/2005 | Takemoto et al. ............ | 606/144 |
| 2007/0162052 A1 | * | 7/2007 | Hashimoto et al. ........... | 606/139 |

FOREIGN PATENT DOCUMENTS

| | | |
|---|---|---|
| JP | 06-054855 | 3/1994 |
| JP | 08-066405 | 3/1996 |
| JP | 2003-225241 | 8/2003 |

OTHER PUBLICATIONS

Japanese Office Action dated Jan. 5, 2010 together with an English translation.
Japanese Office Action (Notice of Allowance) dated Jun. 8, 2010.

* cited by examiner

*Primary Examiner* — Corrine M McDermott
*Assistant Examiner* — Christopher L Templeton
(74) *Attorney, Agent, or Firm* — Scully, Scott, Murphy & Presser, P.C.

(57) ABSTRACT

A ligating apparatus including a thread receiving portion movably disposed at a distal end of an inserting part body. An outer circumference of the thread receiving portion forms the loop holding portion around which a knot forming loop formed from a ligature is disposed. When a first end of the ligature is pulled into the thread receiving portion, the knot forming loop is pushed out of the loop holding portion by a delivery portion of the knot pusher. The knot forming loop is further pushed by the delivery portion along the ligature toward tissue and ligated. Such ligating apparatus is capable of reducing a load on the tissue to be ligated during a ligating operation.

6 Claims, 25 Drawing Sheets

LIGATING APPARATUS

BACKGROUND OF THE INVENTION

1. Field of the Invention

The present invention relates to a ligating apparatus, which is used by inserting into a living organ, to ligate tissues or the like.

Priority is claimed on Japanese Patent Application No. 2006-064023, filed on Mar. 9, 2006, the content of which is incorporated herein by reference.

2. Description of the Related Art

Ligating apparatuses of this type include ones of such constitutions that ligate blood vessels (refer to, for example, U.S. Pat. No. 5,312,423 specification and U.S. Pat. No. 5,336,229 specification). The ligating apparatus has a loop formed of a twisted ligature disposed at the distal end of a tube, and an arm is provided to protrude on the distal side than the loop. The arm has a curved shape so as to be capable of taking in a blood vessel, while an end of the ligature is routed along the arm and fastened onto the distal end of the arm. When the blood vessel is ligated, the blood vessel is housed in the warped portion of the arm and a hook disposed in the tube is moved forward. Then the end of the ligature, which is fastened onto the arm, is hitched with the hook and the hook is retracted so as to release the ligature from the arm and pull it into the tube. Then the tube is retracted and the loop of the ligature disposed at the distal end of a tube is released from the tube, so that the loop turns into a knot. As the ligature is pulled further, the distal end of the arm bends so that the ligature comes off the arm and ligates the blood vessel.

SUMMARY OF THE INVENTION

The invention according to the present invention is a ligating apparatus which includes an inserting part body which is at least partially inserted into a human body, a ligature which forms a knot forming loop disposed at the distal side of the inserting part body, a first fastening portion disposed at the distal side of the inserting part body for fastening the first end of the ligature thereon, a second fastening portion disposed at the distal side of the inserting part body for fastening the second end located opposite to the first end of the ligature thereon, a first fastening portion receptor portion which is provided so as to be movable relative to the first fastening portion and receives the first end that is fastened onto the first fastening portion, a loop holding portion disposed on the first fastening portion receptor portion for holding the knot forming loop, and a knot pusher having a knot delivery portion which is provided so as to be movable relative to the first fastening portion receptor portion and to the inserting part body and, after the first end of the ligature has passed through the inside of the knot forming loop, makes the knot forming loop slide over the first end of the ligature, so as to depart from the distal side of the inserting part body and to move to a part of the organ to be ligated.

Preferably, the knot pusher has a loop delivery portion which is disposed on the proximal end side of the knot forming loop that is disposed on the loop holding portion, and can freely slide along the loop holding portion, so as to move the knot forming loop from the loop holding portion toward the first end side of the ligature while sliding from the proximal end toward the distal end of the loop holding portion.

Preferably, the knot pusher is provided with a thread cutting blade which cuts off the ligature.

Preferably, the knot delivery portion of the knot pusher is constituted to be capable of opening and closing so as to pinch the ligature, and an opening preventing member which makes the knot delivery portion press in closing direction is provided so as to be movable back and forth with respect to the knot pusher.

Preferably, the loop delivery portion is provided with a guide groove which guides the ligature.

Preferably, the loop delivery portion has rings each provided at the distal end of one of a plurality of arms, the rings partially overlapping each other so as to maintain a space through which the ligature is able to pass, and the arms are constituted so as to bias the rings to move in directions away from each other.

BRIEF DESCRIPTION OF THE DRAWINGS

FIG. 34 is a diagram showing the constitution of the ligating apparatus for ligating blood vessel or the like.

DETAILED DESCRIPTION OF THE INVENTION

Figure 1:
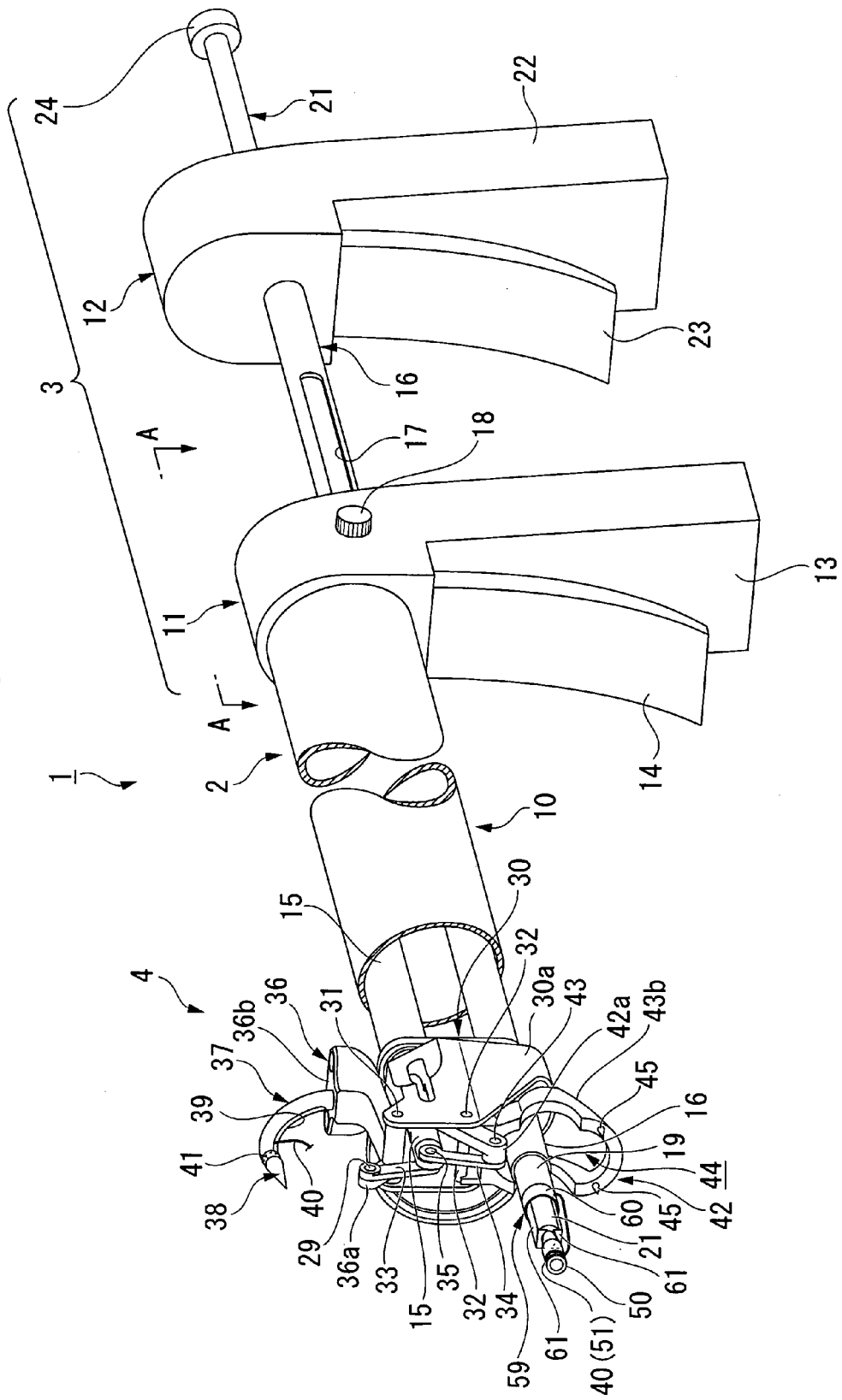
FIG. 1 is a perspective view showing the constitution of the ligating apparatus.

First embodiment of the present invention will now be described in detail with reference to FIG. 1 to FIG. 21.

The ligating apparatus 1 shown in FIG. 1 has an inserting part 2 which is inserted through a port formed in abdominal wall into the human body, while a control portion 3 operated by a surgeon is provided at a proximal end of the inserting part 2 (hereinafter referred to as proximal end) and a manipulation portion 4 which ligates the organ is provided at a distal end of the inserting part 2 (hereinafter referred to as distal end).

The control portion 3 includes a first handle 11 fastened onto the inserting part body 10 of the inserting part 2 and a second handle 12 located at the position nearer to the proximal end side by a predetermined distance from the first handle 11. The first handle 11 is attached to a control portion body 13 in such a manner that an open/close lever 14 can be moved freely. The open/close lever 14 is linked to a rod 15, so that the rod 15 can be moved back and forth by operating the open/close lever 14. A cover sheath 16 comes out of the control portion body 13. As shown in FIG. 1 and FIG. 2, the cover sheath 16 has an elongated hole 17 formed along the longitudinal direction, while the distal end of a lock ring 18 which can be screwed into the control portion body 13 is inserted into the elongated hole 17. The distal end of the lock ring 18 passes through an elongated hole 20 of an arm sheath 19 which passes through the cover sheath 16, and makes contact with the circumference surface of an inner sheath 21, so as to secure the inner sheath 21 with respect to the first handle 11. The second handle 12 has a control portion body 22 and the proximal end of the cover sheath 16 which extends from the first handle 11 is put into the control sportion body 22. The control portion body 22 is provided with an open/close lever 23. The open/close lever 23 is linked to the cover sheath 16, so that the cover sheath 16 can be moved back and forth by operating the open/close lever 23. The inner sheath 21 comes out of the proximal end of the second handle 12, and a knob 24 is fastened onto the proximal end of the inner sheath 21.

The inserting part 2 has an inserting part body 10 of tubular shape, where the rod 15 and the cover sheath 16 are provided in parallel through the inserting part body 10. the Arm sheath 19 is provided movably back and forth in the cover sheath 16. And, the inner sheath 21 is provided movably back and forth in the arm sheath 19.

Figure 2:
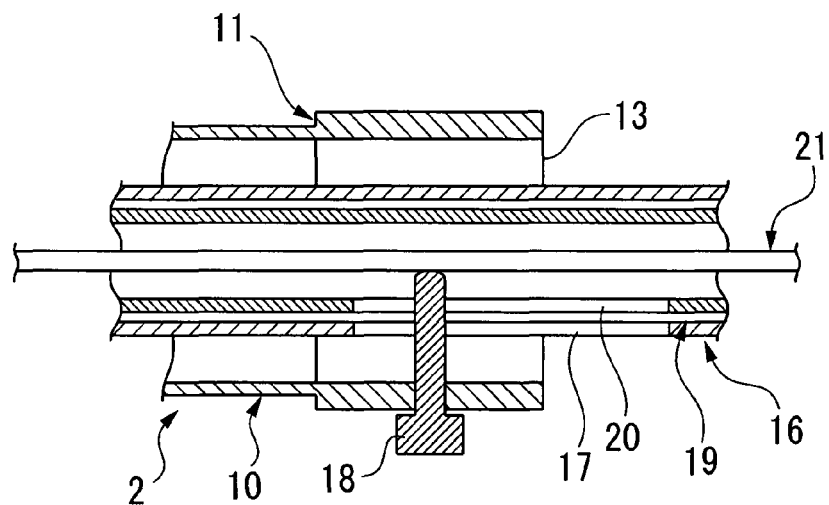
FIG. 2 is a sectional view taken along lines A-A in FIG. 1.
Figure 3:
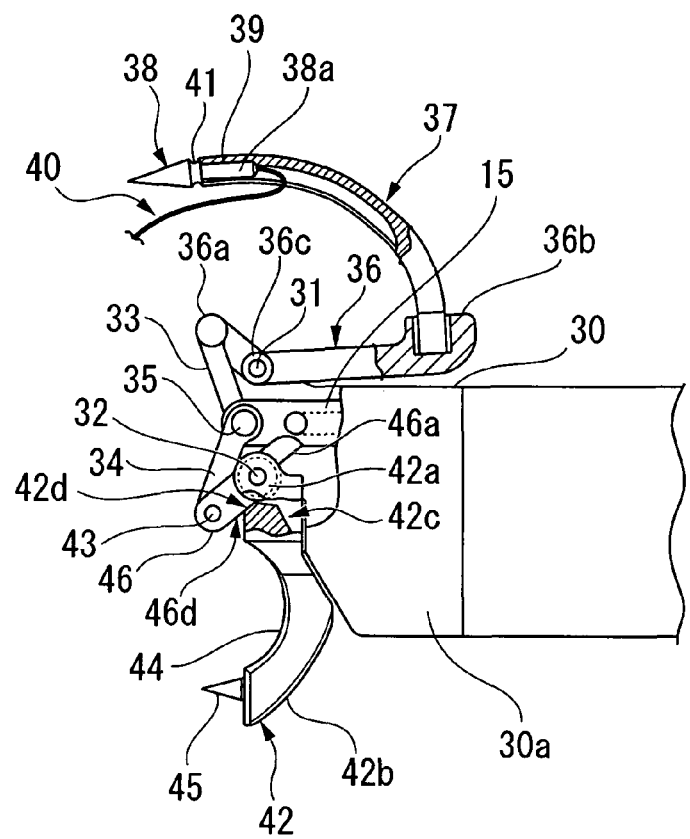
FIG. 3 is an enlarged side view of the distal end of the ligating apparatus.

As shown in FIG. 1 and FIG. 3, the manipulation portion 4 has a support member 30. The rod 15, which is a transmission member, is provided movably back and forth in the support member 30. The support member 30 also has a pair of pins 31, 32 attached thereto in parallel interposing the rod 15 therebetween. At the distal end of the rod 15, one end of a pair of link pieces 33, 34, which constitute an open/close mechanism, are rotatably attached by a pin 35. The other end of the link piece 33 is linked via a pin 29 with one end 36a of the clamp member 36. The clamp member 36 has a bending portion extending from one end 36a to the other end 36b, the bending portion 36c being supported rotatably by the pin 31 on the support member 30. Distance between the bending portion 36c and the other end 36b is larger than the distance between one end 36a and the bending portion 36c. A curved needle 37 is fastened onto the other end 36b of the clamping member 36. The curved needle 37 has a mildly curve shape and the distal end thereof is constituted as a distal end needle portion 38 which is detachable. The distal end needle portion 38 is fixed onto the curved needle 37 by pressing a reduced diameter portion 38a provided on the proximal end side of the needle portion 38 into a hole 39 formed in the curved needle 37. A first end of the ligature 40 is pulled into the distal end needle portion 38 from the reduced diameter portion 38a side. And the distal end needle portion 38 serves as a first fastening member in which the first end of the ligature 40 is fastened. Moreover, an annular concave portion 41 formed in the circumferential direction is provided in a portion of the distal end needle portion 38 which is exposed from the curved needle 37.

The link piece 34, on the other hand, is linked rotatably to one end of a force accumulating portion 46 by a pin 43. The force accumulating portion 46 is supported rotatably on the support member 30 by a pin 32 at a position between the one end and the other end, with a contact surface 46a formed on the other end. One end 42a of the clamping member 42 is penetrated by the pin 32 rotatably. The other end 42b of the clamping member 42 has annular shape formed by an opening portion 44, and two needles 45 are secured at positions away from the pin 32. A contact surface 42c is extended on one end 42a of the clamping member 42 so as to be capable of making contact with the contact surface 46a of the force accumulating portion 46 side. A pair of clamping members 36, 42 opens as the rod 15 moves forward and closes as the rod 15 moves backward. When the clamping member 42 opens, a contact surface 46d of the force accumulating portion 46 which rotates as the rod 15 moves forward makes contact with a contact surface 42d of the clamping member 42, thereby making the clamping member 42 rotate around the pin 32. When the pair of clamping members 36, 42 closes, the curved needle 37 of the claming member 36 passes through the opening portion 44 of the clamping member 42 and protrudes toward the proximal end.

Figure 4:
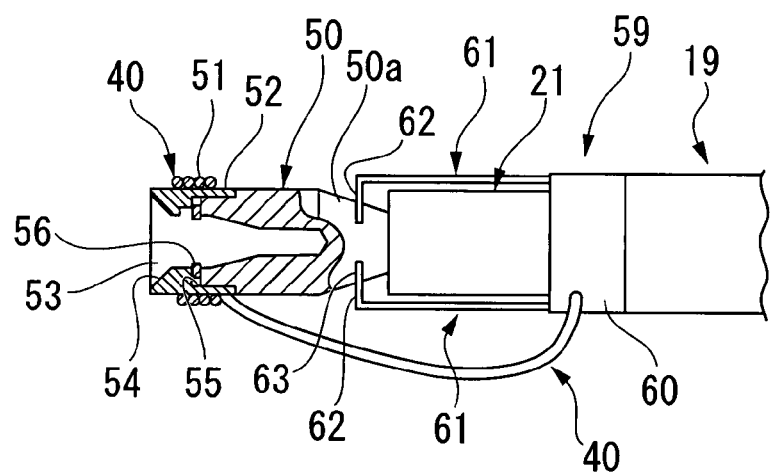
FIG. 4 is a diagram showing the thread receiving member and the knot pusher.

The support member 30 swells substantially in parallel in a direction where the clamping member 42 side substantially intersects at right angle with the axial line. The cover sheath 16 passes through the swelling portion 30a. The arm sheath 19 protrudes from the distal end of the cover sheath 16, and the inner sheath 21 protrudes from the distal end of the arm sheath 19. A thread receiving portion 50 (first fastening portion receptor portion) is fastened onto the distal end of the inner sheath 21. As shown in FIG. 4, the thread receiving portion 50 has a tapered portion 50a in which the diameter increases toward the distal end and a tubular shape portion extends further to the distal end. The knot forming loop 51 is formed by winding the ligature 40 around the circumference of the tubular shape portion. The loop 51 is used in forming a knot during ligating operation, and the circumference of the thread receiving portion 50 serves as the loop holding portion 52 which holds the knot forming loop 51 that forms a knot.

Moreover, the thread receiving portion 50 also has an insertion hole 53 which opens toward the distal end thereof. The insertion hole 53 has a tapered surface 54 where the diameter decreases from the opening at the distal end. A groove 55 is formed at a position located on the proximal end side than the tapered surface 54 in which a spring 56 is inserted. As shown by dashed line in FIG. 4, the spring 56 is bended in U shape except for the end portion inserted into the groove 55. The end portions are biased to move closer to each other due to the U shape, and the distance between the ends of the spring 56 is smaller than the maximum diameter of the distal end needle portion 38 when no load is applied. The size of the insertion hole 53 is substantially equal to the outer diameter of the distal end needle portion 38 shown in FIG. 1, and the insertion hole serves as a needle receiving portion which is capable of receiving and recovering the distal end needle portion 38 in the thread receiving portion 50.

Figure 5:
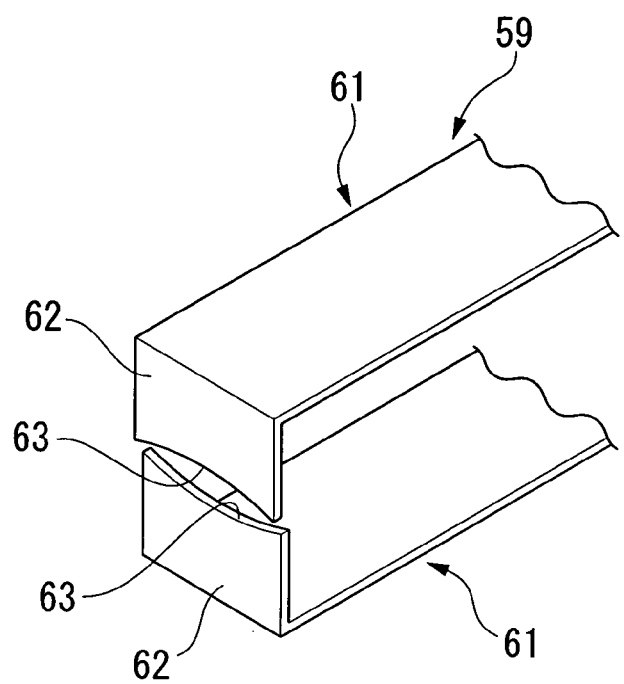
FIG. 5 is a perspective view of the distal end portion of the knot pusher.

A knot pusher 59 is fastened onto the distal end of the arm sheath 19 which covers the inner sheath 21. The knot pusher 59 has a pusher holder 60 of tubular shape. The pusher holder 60 is a second fastening portion whereon the second end of the ligature 40, which has formed the knot forming loop 51, is fastened. A pair of pusher arms 61 is further secured onto the pusher holder 60. The pusher arms 61 are made of an elastic material and are constituted such that they extend along the axial direction toward the distal end and bend so as to face each other to form a delivery portion 62. The delivery portion 62, in the initial state, makes contact with the outer circumference of the thread receiving portion 50 so as to pinch the tapered portion 50a. As the knot pusher 59 moves forward, the delivery portion 62 serves as the loop delivery member so as to push out the knot forming loop 51. The delivery portion 62 has arc shaped notches on the end portions which oppose each other, as shown in FIG. 5. A space formed by the notches 63 defines the dimension allowing the ligature 40 to pass therethrough when the pusher arm 61 restores the original state by the self-restoring force so that the delivery portions 62 make contact with each other. Since the radius of curvature of the curved surface of the notch 63 is larger than the outer diameter of the loop holding portion 52, the knot pusher 59 always keeps contact with the outer circumference of the loop holding portion 52.

The ligature 40 is preferably formed from Nylon®, polyester, silk, fluororesin or bioabsorbable material in monofilament or twisted thread. The knot formed by the knot forming loop 51 is preferably such as Grinch knot or Roders knot so that the knot itself can be movable.

The operation according to this embodiment will now be described.

Figure 6:
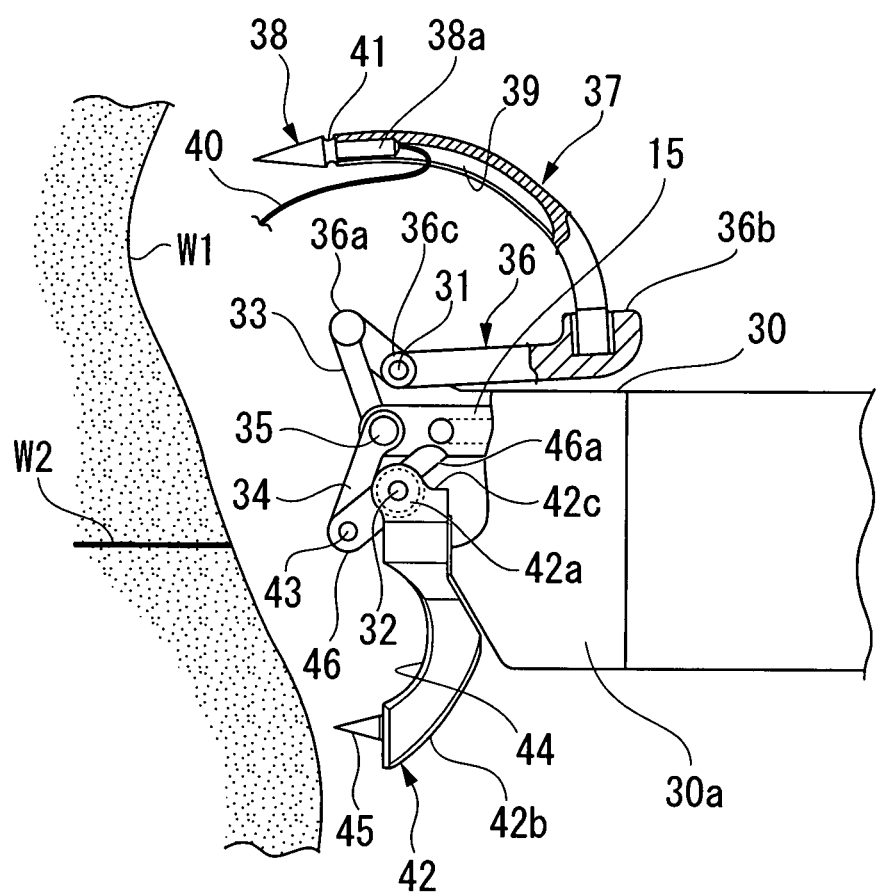
FIG. 6 is a diagram which explains the procedure
Figure 7:
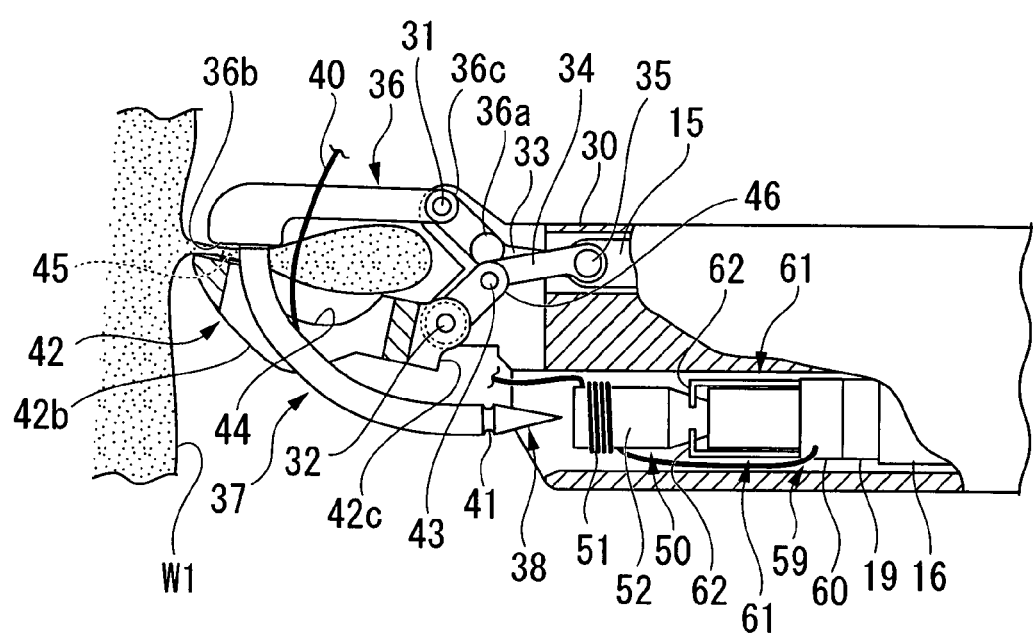
FIG. 7 is a diagram showing the curved needle penetrated the tissue.

A laparoscope is inserted through a port formed in the abdominal wall of a patient, to observe within the abdominal cavity and identify the organ to be ligated. The ligating apparatus 1 is inserted into the abdominal cavity through another port, and the manipulation portion 4 is positioned so as to face the organ to be ligated. When a tissue W1, on which an opening W2 is formed, is to be ligated as shown in FIG. 6, the open/close lever 14 of the first handle 11 is held so as to move the rod 15 backward. Then a pair of clamping members 36, 42 linked to the distal end of the rod 15 via a link mechanism closes as shown in FIG. 7.

At this time, the curved needle 37 of the clamping member 36 is inserted to the tissue W1, which neighbors on one side of the opening W2, and the tissue W1 around the inserted point is hauled. At this time, since the clamping member 42 is pressed against the tissue W1 on the other side of the opening W2, the curved needle 37 penetrates the tissue W1 so as to traverse the opening W2, without allowing the tissue W1 around the opening W2 to slip out.

Figure 8:
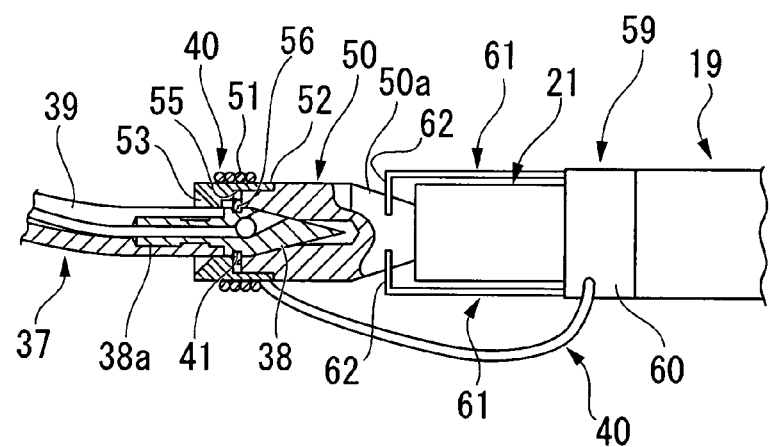
FIG. 8 is a diagram showing the distal end needle portion recovered in the thread receiving member.
Figure 9:
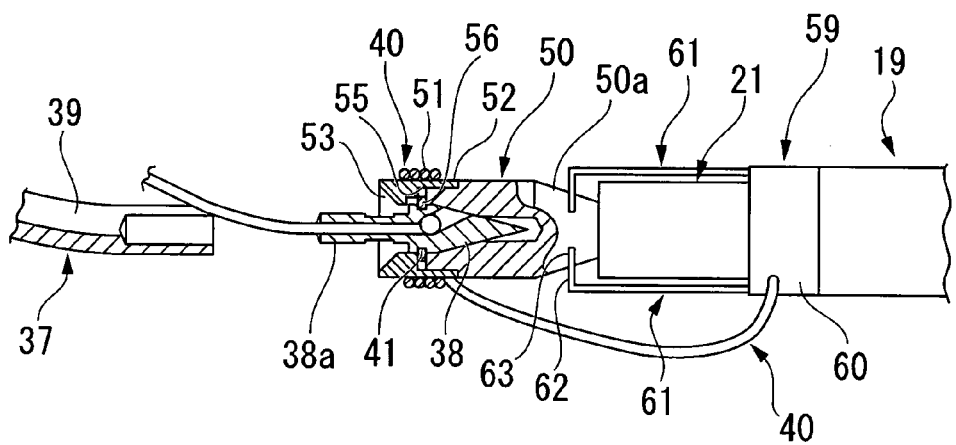
FIG. 9 is a diagram showing the state of the curved needle being pulled back and the distal end needle portion being placed in the thread receiving member.
Figure 10:
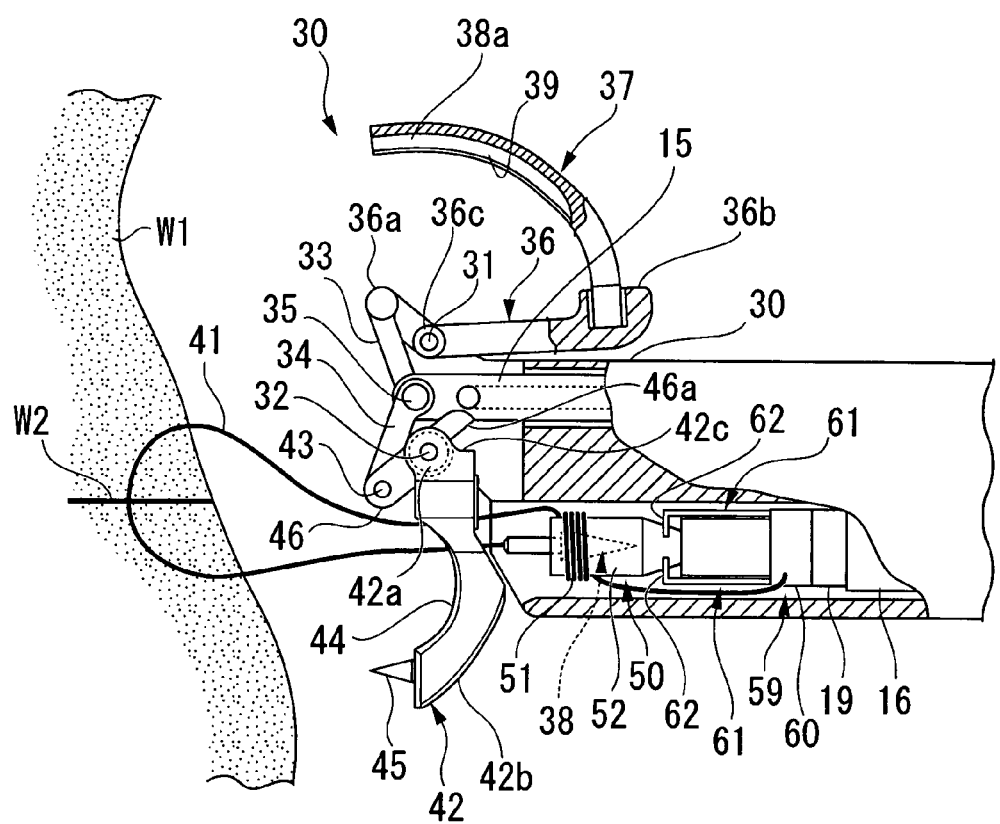
FIG. 10 is a diagram showing the state of the curved needle being removed from the tissue with only the ligature remained in the tissue.

When the curved needle 37 penetrates the tissue W1, the second handle 12 and the knob 24 are moved forward with the lock ring 18 (refer to FIG. 1) being loosened, so that the thread receiving portion 50 moves forward and the distal end needle portion 38 is recovered in the insertion hole 53. At this time, the distal end needle portion 38 advances while making the ends of the spring 56 open in the insertion hole 53. When the distal end needle portion 38 makes contact with the inner circumferential surface of the insertion hole 53, the concave portion 41 of the distal end needle portion 38 enters the position where the groove 55 is formed. Then as shown in FIG. 8, the end portion of the spring 56 in the groove 55 restores to original state and enters the concave portion 41. Thus the distal end needle portion 38 is fastened onto the thread receiving portion 50. Then as the second handle 12 and the knob 24 are moved backward away from the first handle 11, the thread receiving portion 50 moves backward. Accordingly, the distal end needle portion 38 fastened onto the thread receiving portion 50 disengages from the curved needle 37 as shown in FIG. 9. Then the open/close lever 14 of the first handle 11 is operated so as to open the pair of clamping members 36, 42. This makes the curved needle 37 remove from the tissue W1 as shown in FIG. 10. As a result, the first end of the ligature 40 is pulled into the thread receiving portion 50 and extends therefrom toward the tissue W1 to penetrate the tissue W1 so as to traverse the opening W2 and returns to the thread receiving portion 50 to reach the second fastening portion through the knot forming loop 51 disposed in the loop holding portion 52 of the thread receiving portion 50.

Figure 11:
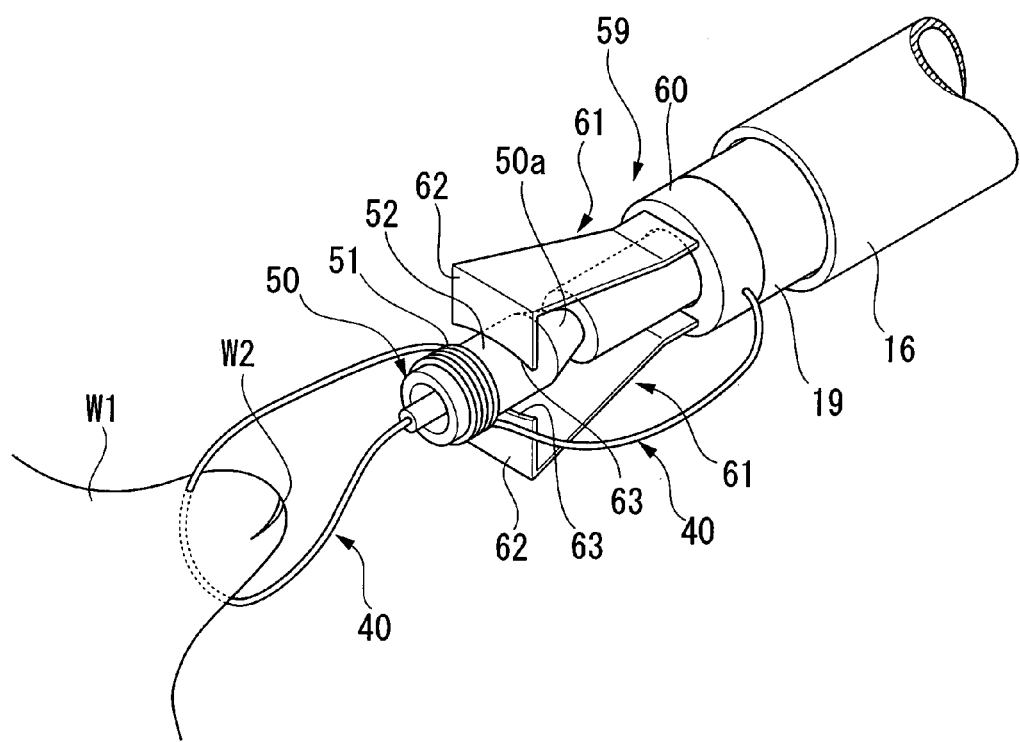
FIG. 11 is a diagram explaining the process in which the knot pusher is advanced to push out the knot forming loop.
Figure 12:
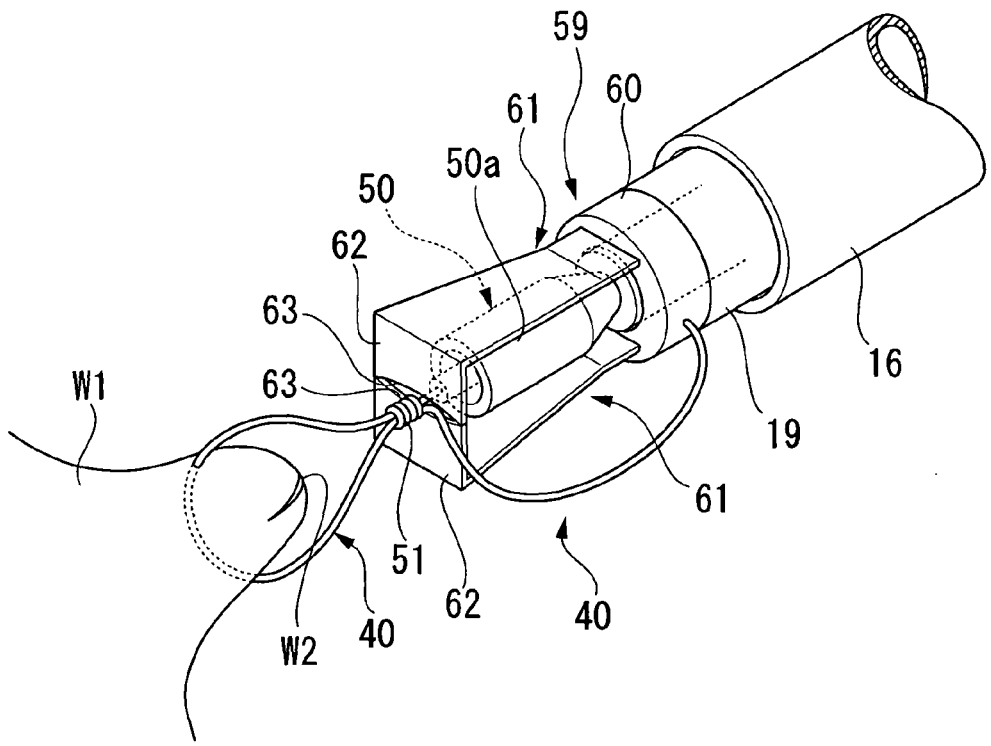
FIG. 12 is a diagram explaining the process in which the knot forming loop which has been pushed out is moved toward the tissue.

After linking the control portion body 13 and the inner sheath 21 by means of the lock ring 18 of the first handle 11, the second handle 12 is moved forward so as to approach the first handle 11. The knot pusher 59 moves forward while the thread receiving portion 50 remains stationary as shown in FIG. 11. The pusher arm 61 moves forward expanding along the tapered portion 50a, and makes contact with the knot forming loop 51 from the proximal end side. As the knot pusher 59 is moved further forward, the knot forming loop 51 is pushed out from the distal end of the loop holding portion 52. As the knot pusher 59 moves forward beyond the loop holding portion 52 as shown in FIG. 12, the restoring force of the knot pusher 59 makes itself restore in closing direction, and the ligature 40 is passed between the notches 63. Since the notch 63 is larger than the outer diameter of the reduced diameter portion 38a, the delivery portion 62 can move forward without being hitched by the reduced diameter portion 38a.

Figure 13:
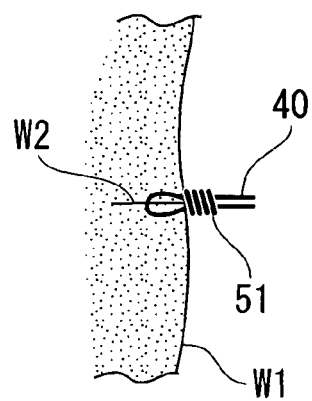
FIG. 13 is a diagram showing the state of the tissue being ligated.

Since the knot forming loop 51 is located on the tissue W1 side than the knot pusher 59, when the second handle 12 is moved further forward, the delivery portion 62 of the knot pusher 59 pushes out the knot forming loop 51 along the ligature 40 toward the tissue W1. As one end (first fastening portion) of the ligature 40 is moved relatively backward together with the thread receiving portion 50, the knot forming loop 51 is gradually tightened to become a knot. The delivery portion 62 becomes a knot delivery portion which pushes out the knot. In this way, as the knot formed of the knot forming loop 51 is pressed against the tissue W1 by the delivery portion 62, the tissue W1 is ligated in constricted state. Then extra portion of the ligature 40 is cut off by means of scissors or the like which is not shown. The ligature 40 is left in place in such a state that the opening W2 is ligated as shown in FIG. 13.

According to this embodiment, since the knot pusher 59 which pushes the knot forming loop 51 out of the thread receiving portion 50 is provided, the knot forming loop 51 is pushed out without applying a load on the tissue W1. Moreover, since the knot forming loop 51 is pressed by the knot pusher 59 against the tissue W1 so as to constrict the tissue W1, load on the tissue W1 can be reduced when constricting the tissue W1. Also because the tapered portion 50a which expands toward the distal end of the thread receiving portion 50 is provided and the delivery portion 62 of the knot pusher 59 is disposed on the tapered portion 50a, the knot pusher 59 is prevented from protruding outside in radial direction in the initial state, and the manipulation portion 4 can be prevented from becoming larger.

Since the notches 63 are provided in the delivery portion 62 which functions as both the loop delivery portion and the knot delivery portion, the delivery portion 62 reliably makes contact with the loop holding portion 52 and, after pushing the knot forming loop 51 out of the loop holding portion 52, the ligature 40 does not come off the knot pusher 59 so that the tissue W1 can be reliably ligated with the ligature 40.

Figure 14:
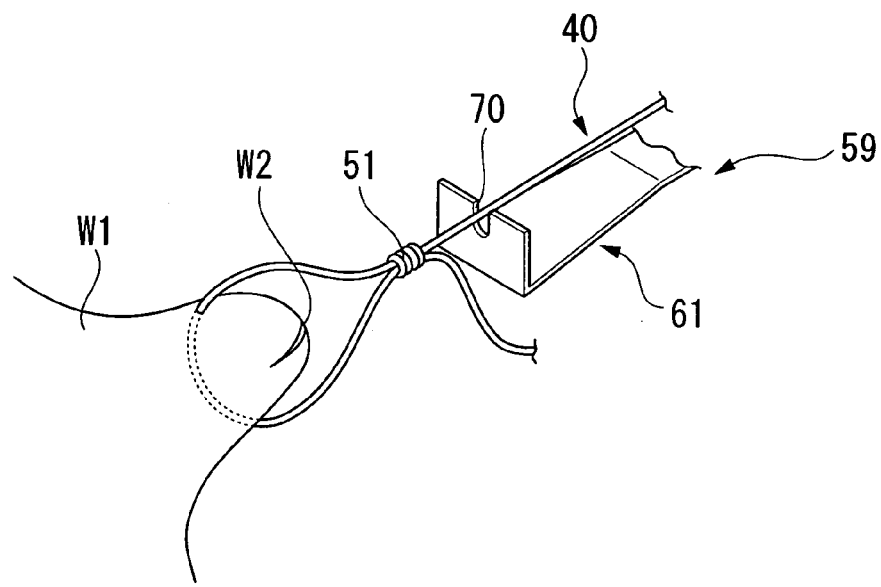
FIG. 14 is a diagram showing a case where only one knot pusher is provided.
Figure 15:
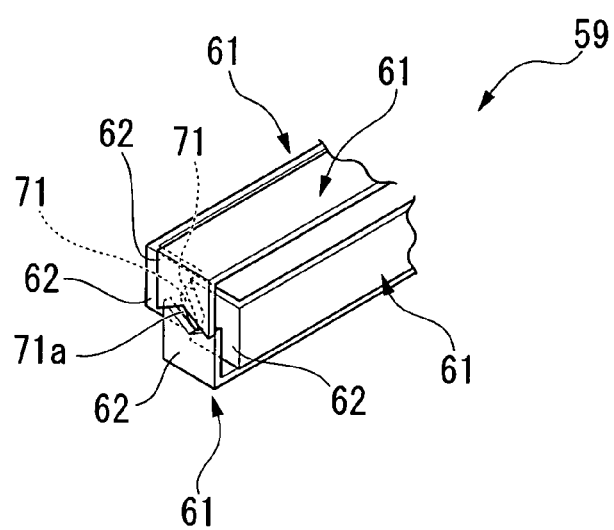
FIG. 15 is a diagram showing a case where four knot pushers are provided.

The knot pusher 59 may have such a constitution that has only one pusher arm 61 as shown in FIG. 14. In this case, the ligature 40 can be prevented from coming off, by forming a deep groove 70 in the delivery portion 62 of the pusher arm 61 so that the ligature 40 can pass through the groove 70. The knot pusher 59, in contrast, may have three or more pusher arms 61. In case four pusher arms 61 are provided, for example, as shown in FIG. 15, the pusher arms 61 are disposed at equal intervals in the circumferential direction, so that the ligature 40 is passed between the delivery portions 62 provided at the distal ends of the pusher arms 61. The ligature 40 can be prevented from coming off more reliably by increasing the number of the pusher arms 61. The delivery portion 62 has a V groove 71 formed in a direction facing the ligature 40 (axial line), and the ligature 40 passes through a space 71a which is formed by overlapping V grooves 71. The space 71a is smaller than the knot forming loop 51. Here, the notch 63 or the groove 70 may also be used instead of forming the V groove 71.

Figure 16:
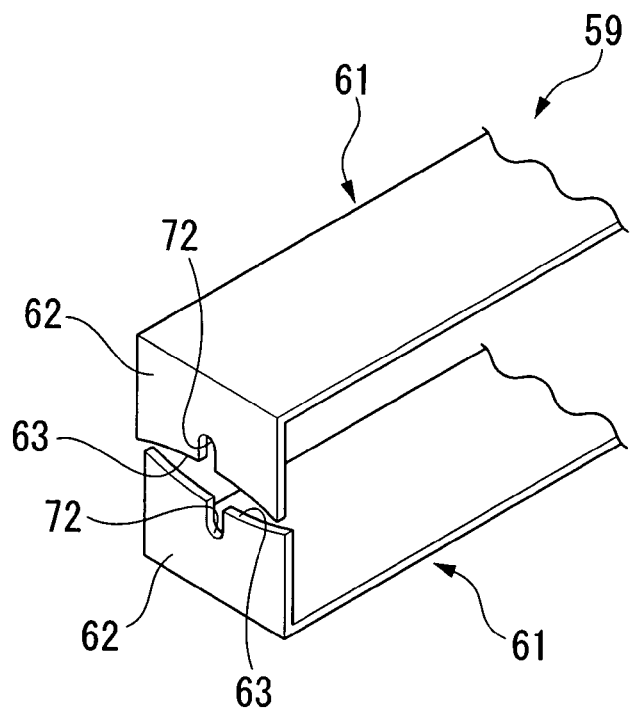
FIG. 16 is a diagram showing a notch and a groove being formed at the distal end of the knot pusher.
Figure 17:
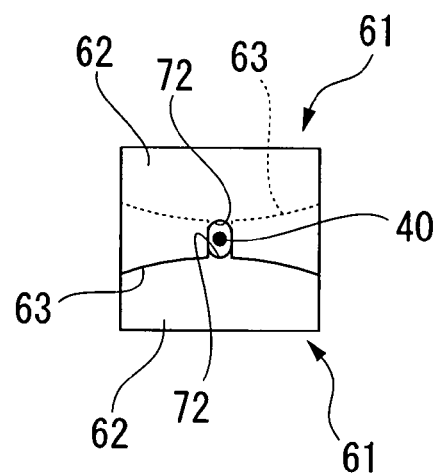
FIG. 17 is a front view of the knot pusher of FIG. 16.
Figure 18:
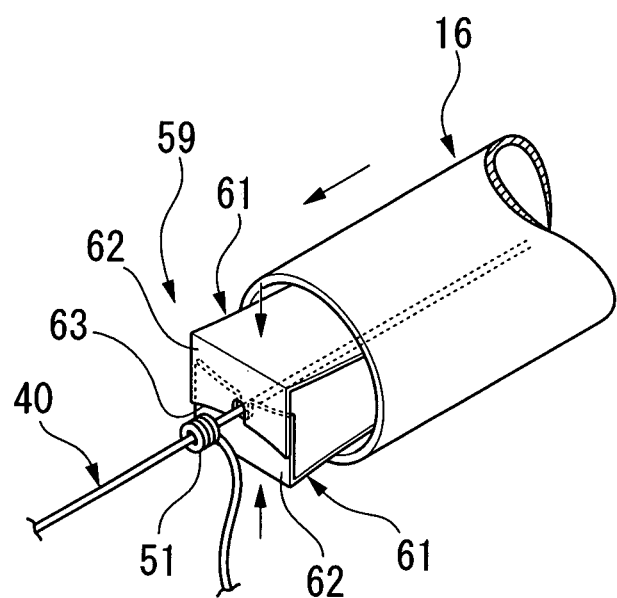
FIG. 18 is a diagram showing a case where the cover sheath is used as the opening preventing member.

A guide groove 72 may also be formed in the delivery portion 62 which has the notch 63 as shown in FIG. 16. The guide groove 72 is provided in the center of the notch 63 and is formed in such a shape that allows the ligature to pass through and to be guided therethrough. As shown in FIG. 17, the pusher arms 61, in the natural state, form the guide groove 72 as an elongated hole by overlapping the delivery portions 62 with each other. By passing the ligature 40 through the elongated hole formed by the guide groove 72, the ligature 40 is prevented from coming off the pusher arm 61. When the outer diameter of the cover sheath 16 is made smaller than the width of the pusher arm 61 in the opening-closing direction as shown in FIG. 18, it is possible to prevent the pusher arm 61 from expanding by moving forward the cover sheath 16. In this case, the cover sheath 16 serves as the opening prevention member of the knot pusher 59. The ligature 40 can be prevented more surely from coming off the pusher arm 61 by moving the cover sheath 16 forward and pressing the pusher arm 61 in closing direction. To move the cover sheath 16 forward, the open/close lever 23 of the second handle 12 may be operated.

Figure 19:
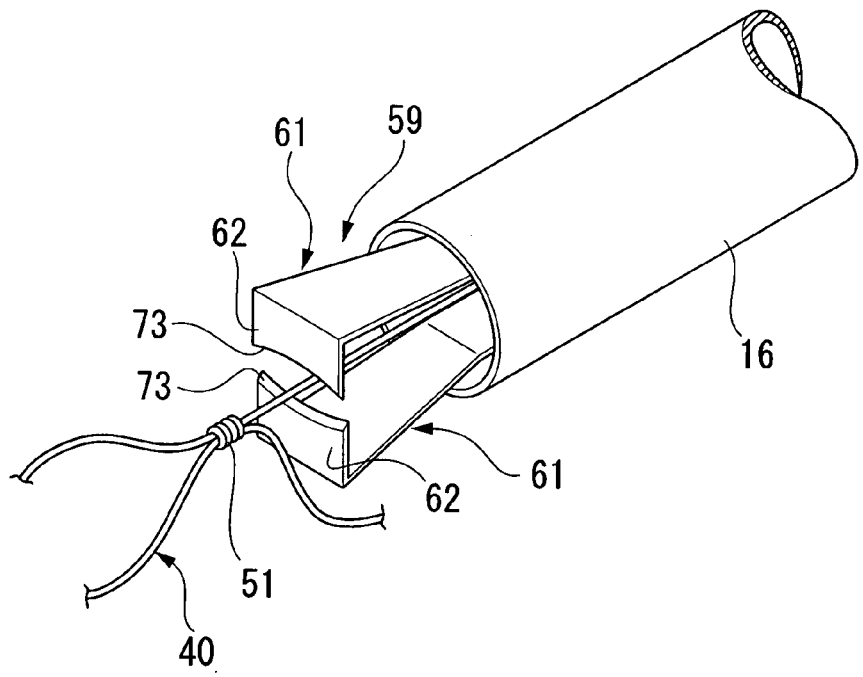
FIG. 19 is a diagram showing a case where the thread cutting blade is provided at the distal end of the knot pusher.
Figure 20:
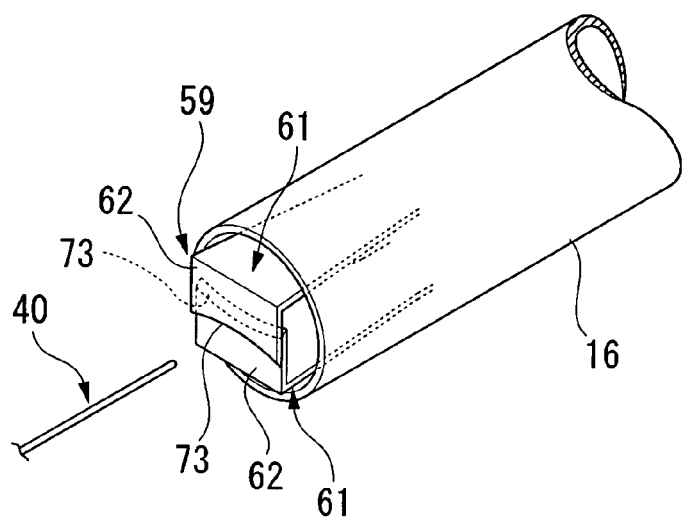
FIG. 20 is a diagram showing the state of the ligature being cut off by the thread cutting blade.

As shown in FIG. 19, a thread cutting blades 73 of arc shape may be formed in the delivery portion 62 of the knot pusher 59. When no external force is applied, the thread cutting blades 73 form such a space that allows the ligature 40 to pass therethrough without cutting the ligature 40, but can hold the knot forming loop 51. After constricting the tissue W1 with the ligature 40, the cover sheath 16 is moved forward. The ligature 40 is cut off by pressing the pusher arms 61 so as to bring them closer to each other so that the thread cutting blades 73 overlap with each other as shown in FIG. 20. This constitution makes it possible to carry out a series of operations up to cutting of the ligature 40 without inserting other cutting tool into the human body.

Figure 21:
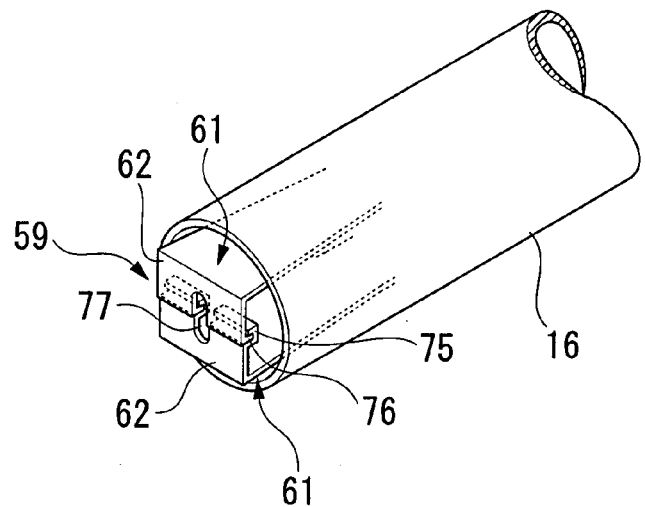
FIG. 21 is a diagram showing a constitution where the distal ends of the knot pushers can engage with each other.

Such a constitution may also be employed as shown in FIG. 21 in which a convex portion 75 is provided on the end portion of one delivery portion 62 and a concave portion 76, which is capable of engaging with the convex portion 75, is provided on the end portion of the other delivery portion 62. While the delivery portions 62 of the knot pusher 59 are apart from each other in the initial state, the convex portion 75 of the delivery portion 62 engages with the concave portion 76 so as to lock the delivery portions 62 with each other, when the cover sheath 16 is moved forward and pressing the knot pushers 59 in closing directions with each other. Thus the ligature 40 which passes through the elongated hole 77 formed in the center is prevented from coming off.

Figure 23:
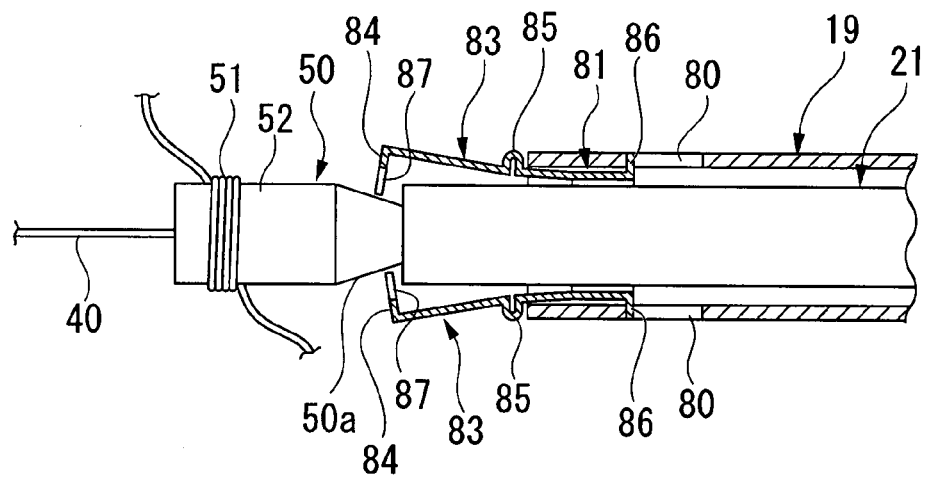
FIG. 23 is a sectional view showing the knot pusher mounted on the arm sheath.
Figure 24:
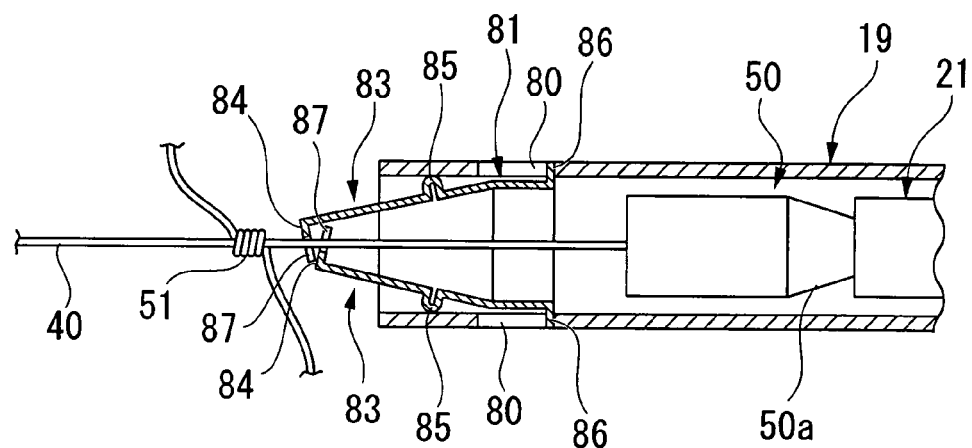
FIG. 24 is a diagram showing the arrangement of the knot pusher when the knot forming loop is pressed by the knot pusher.

Second embodiment of the present invention will now be described with reference to FIG. 22 to FIG. 24. This embodiment differs from the first embodiment in the constitution of the knot pusher having the knot delivery portion. Accordingly, constituent components identical with those of the first embodiment are denoted with the same reference numerals, and identical descriptions will be omitted.

Figure 22:
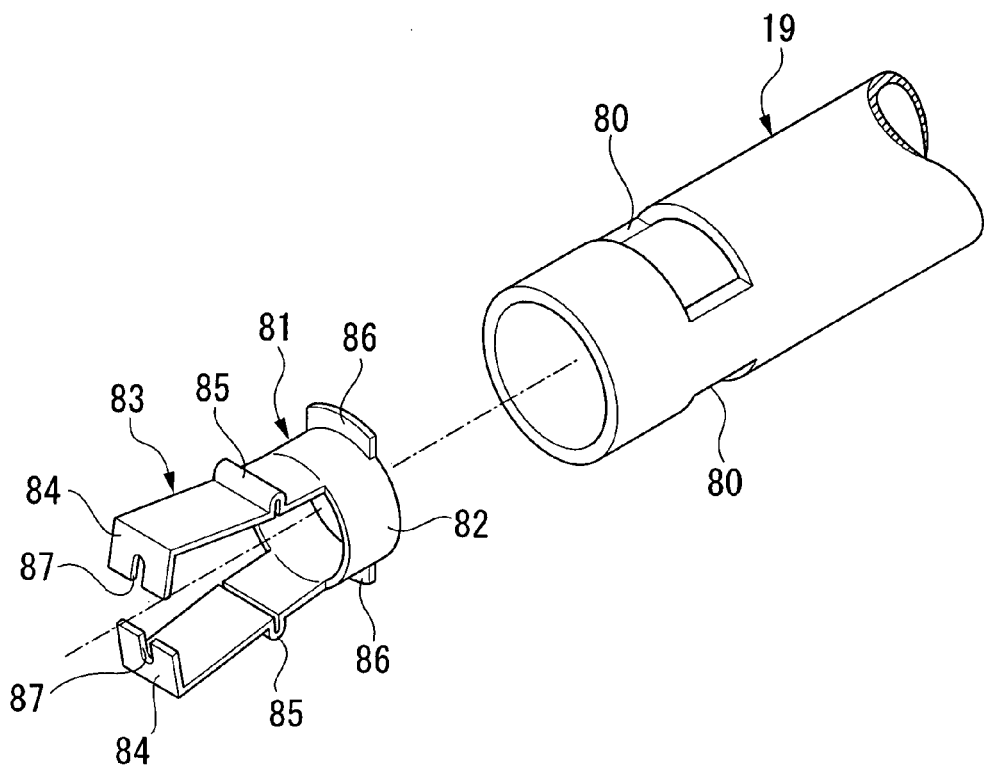
FIG. 22 is a diagram showing a constitution where the knot pusher and the arm sheath are provided separately.

Two slits 80 are formed in parallel in the distal end of the arm sheath 19, as shown in FIG. 22. The slits 80 are located on each of the opposing sides of the arm sheath and are provided to extend in the direction of axial line. The knot pusher 81 engages with the arm sheath 19. The knot pusher 81 has two pusher arms 83 extending in parallel from the tubular base portion 82. Distal end of the pusher arms 83 are bent so as to form delivery portions 84. The delivery portions 84 functions as both the loop delivery portion and the knot delivery portion. Projections 85 projecting outside are formed between the delivery portions 84 and the proximal end of the pusher arms 83. The base portion 82 of the knot pusher 81 has two claws 86 formed thereon projecting outside in radial direction. The knot pusher 81 is made of an elastic material molded in such a manner that the delivery portions 84 overlap with each other in the natural state. When the claws 86 are engaged on the distal end of the slits 80 as shown in FIG. 23, the projections 85 make contact with the distal end of the arm sheath 19, and the delivery portions 84 make contact with the tapered portion 50a of the thread receiving portion 50.

When the knot forming loop 51 is pushed out by the knot pusher 81, the arm sheath 19 is moved forward. As the projections 85 are pressed by the distal end of the arm sheath 19, the pusher arm 83 moves forward, and the delivery portion 84 moves forward while keeping contact with the circumference of the thread receiving portion 50 so as to push the knot forming loop 51 out of the distal end of the thread receiving portion 50. The arm sheath 19 is further moved forward so as to move the whole of the knot pusher 81 beyond the thread receiving portion 50. As the thread receiving portion 50 which has been biasing the knot pushers 81 toward the opening directions is taken away as shown in FIG. 24, the pusher arms 83 close so that the delivery portions 84 overlap with each other. The ligature 40 is passed through the elongated hole formed by the grooves 87 of the delivery portions 84. The closing operation of the pusher arm 83 and the operation of pulling in the thread receiving portion 50 make the knot pusher 81 move until the claws 86 make contact with the proximal end of the slit 80, so that the projections 85 are pulled into the arm sheath 19. Inner circumferential surface of the arm sheath 19 functions as the opening prevention member which presses the pusher arms 83 to prevent them from opening by making contact with the projections 85. As the arm sheath 19 is moved forward in this state, the knot pusher 81 moves forward as if it is pressed by the claws 86. Accordingly, the delivery portions 84 bring the loop 51 toward the tissue and the tissue is ligated.

According to this embodiment, the arm sheath 19 functions as the opening prevention member which presses the pusher arms 83 in the closing direction, the pusher arms 83 are prevented from opening. Therefore, the ligature 40 can be prevented from coming off the knot pusher 81 with a simple constitution. Since the knot pusher 81 can be detached from the arm sheath 19, the component can be easily cleaned. Other effects of this embodiment are similar to those of the first embodiment.

Third embodiment of the present invention will now be described with reference to FIG. 25 to FIG. 33. This embodiment differs from the foregoing embodiments in that the thread receiving portion which also functions as the loop holding portion is constituted in a form of a cartridge. Therefore, constituent components identical with those of the foregoing embodiments are denoted with the same reference numerals, and identical descriptions will be omitted.

Figure 25:
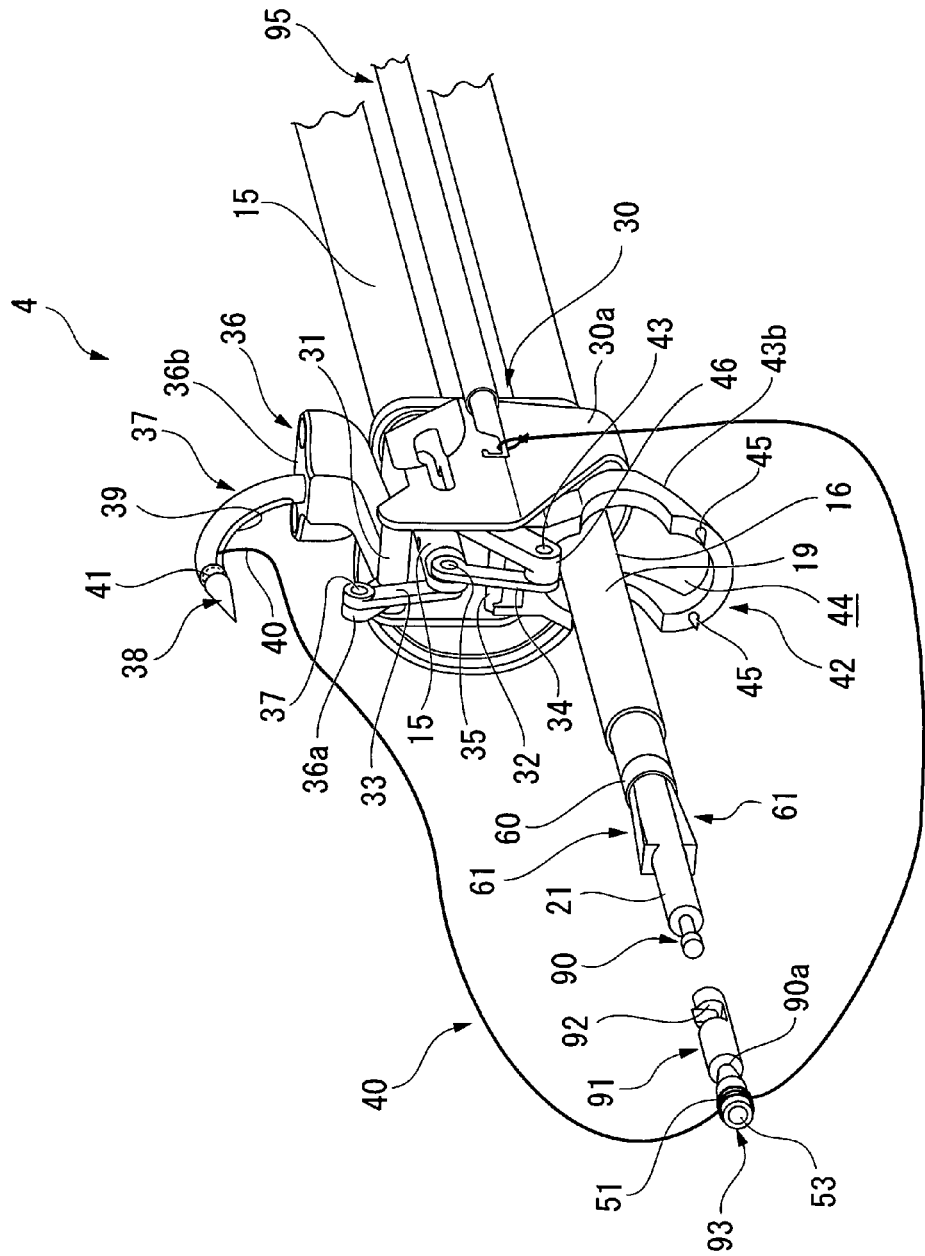
FIG. 25 is a diagram showing a constitution where the thread receiving portion is provided detachably.
Figure 26:
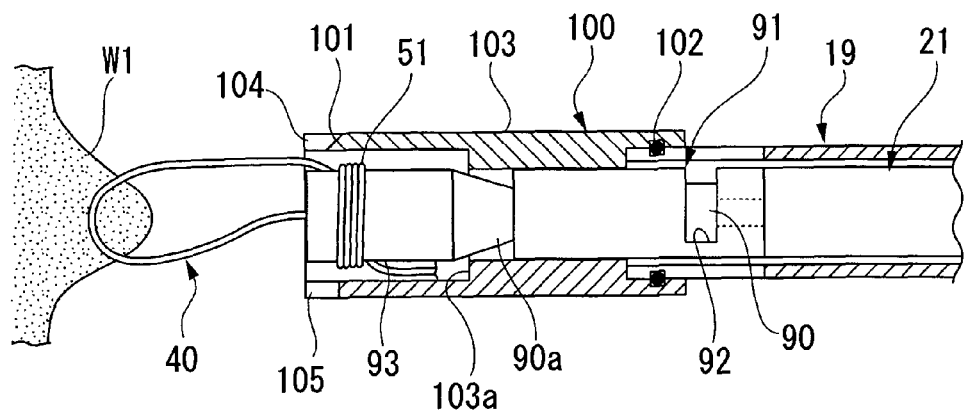
FIG. 26 is a diagram showing the V groove formed at the distal end of the knot pusher.

A joint portion 90 is fixed at the distal end of the inner sheath 21, as shown in FIG. 25. The joint portion 90 has a diameter smaller than that of the inner sheath 21 with the distal end thereof expanding in a disk shape. A thread receiving cartridge 91 (thread receiving portion) is mounted on the joint portion 90. A notch 92, which recovers the joint portion 90, is formed on the thread receiving cartridge 91. On the distal side of the thread receiving cartridge 91, a tapered portion 90a is formed, and further to the distal side, a loop holding portion 93 is formed. The knot forming loop 51 is disposed around the outer circumference of the loop holding portion 93. Second end of the ligature 40 which forms the knot forming loop 51 is fastened to a second fastening portion 95. A hook is provided on the distal end of the second fastening portion 95 and is disposed in parallel to other sheaths 16, 19 and 21 of the inserting part 2. A closed loop formed at the end of the ligature 40 is hitched on the hook.

According to this embodiment, the thread receiving cartridge 91 is mounted on the inner sheath 21 before inserting the ligating apparatus 1 into a human body. The knob 24 located at the rear end of the second control portion 3 is moved forward so that the inner sheath 21 moves forward and the notch 92 is locked onto the joint portion 90. When the thread receiving cartridge 91 is locked, the knob 24 is moved backward and the joint portion of the thread receiving cartridge 91 is pulled into the arm sheath 19. Thus the thread receiving cartridge 91 is prevented from coming off. When the end of the ligature 40 is hitched on the second fastening member 95, the procedure is started. The operation that follows is the same as that in the first embodiment. When the procedure is completed, the inner sheath 21 is moved forward thereby exposing the thread receiving cartridge 91. The thread receiving cartridge 91 which has been used is removed by moving the thread receiving cartridge 91 in the direction perpendicular to the axial line. To carry out another ligation continuously, a new thread receiving cartridge 91 is mounted in the same manner as described above.

According to this embodiment, it is easier to attach and replace the members necessary in ligation by mounting and detaching the thread receiving cartridge 91 which includes the loop holding portion 93. Especially, when a plurality of portions of an organ is ligated, the procedure can be carried out quickly. Other effects of this embodiment are similar to those of the foregoing embodiments.

Figure 27:
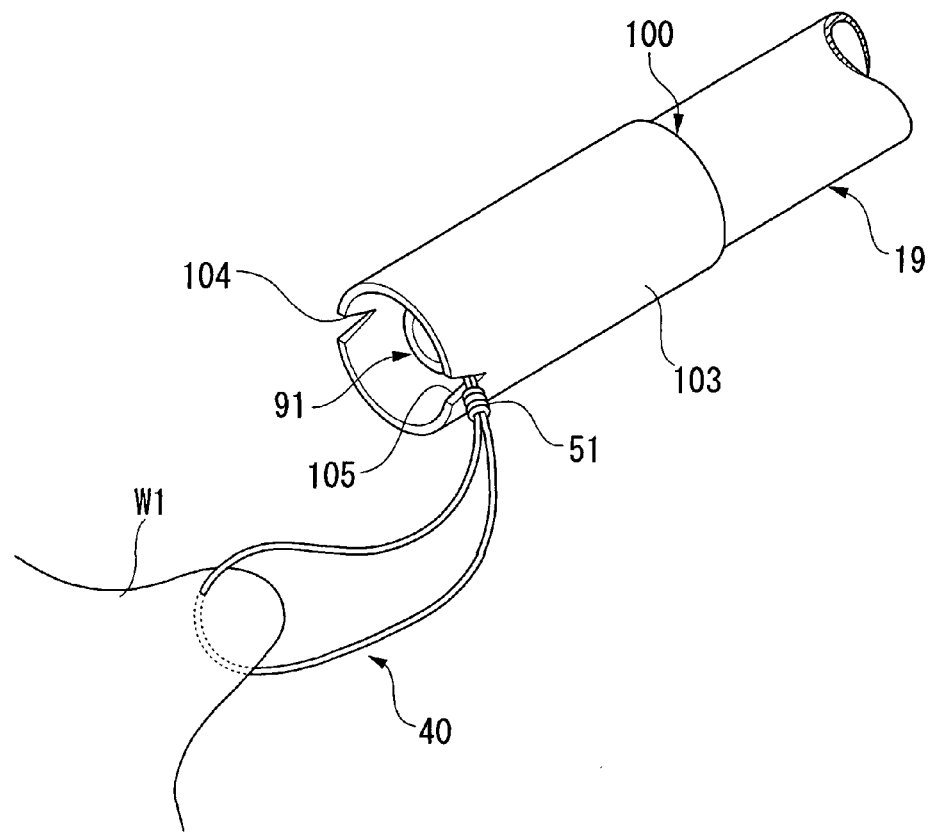
FIG. 27 is a diagram showing the knot forming loop being hooked on one of the V grooves and moved.
Figure 28:
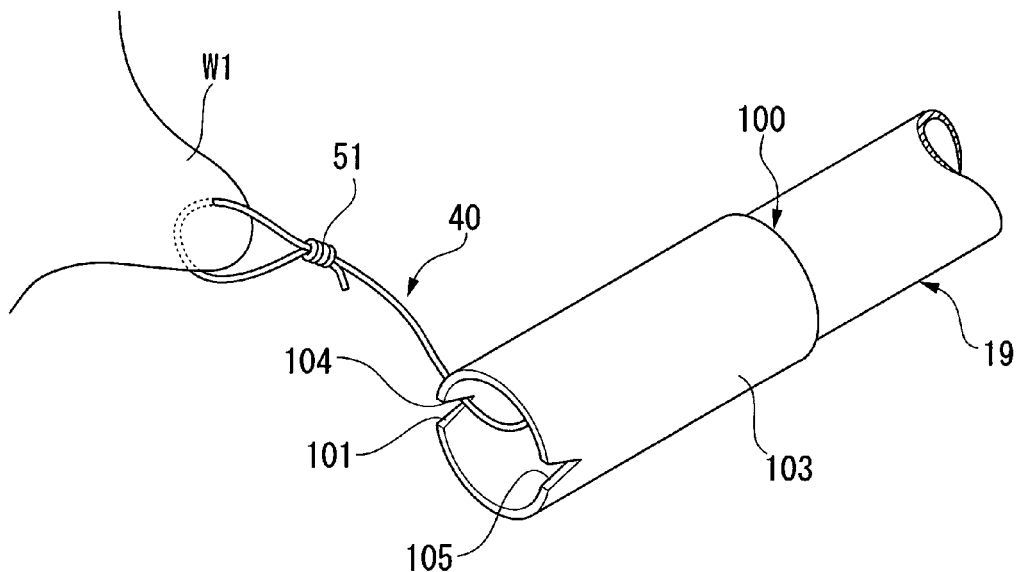
FIG. 28 is a diagram showing the ligature being cut off by the other V groove.
Figure 29:
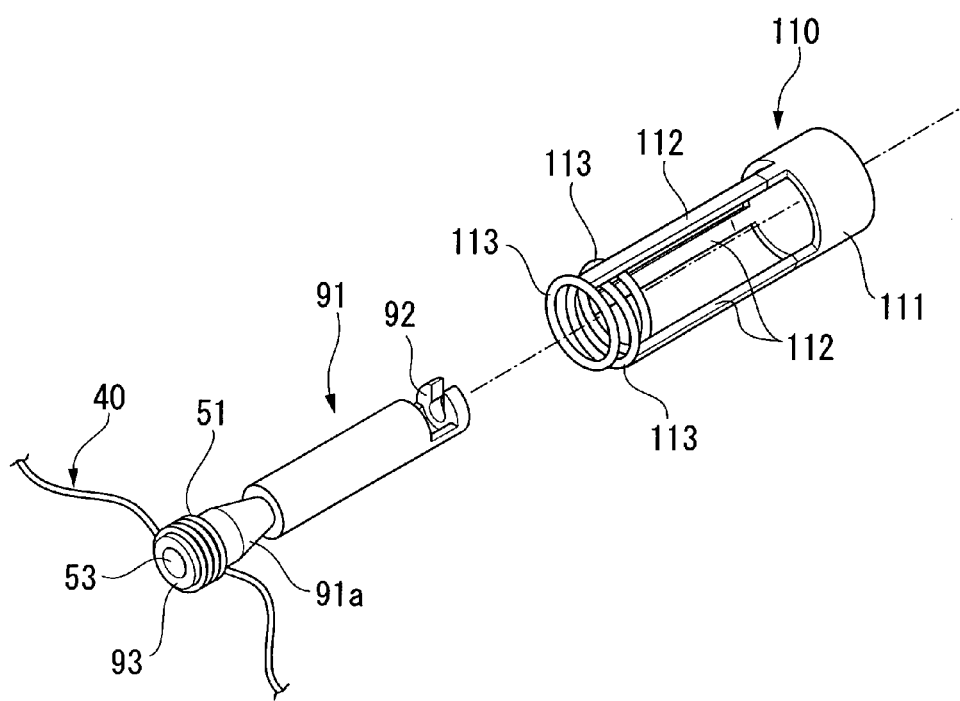
FIG. 29 is a diagram showing the rings provided at the distal end of the knot pusher.
Figure 30:
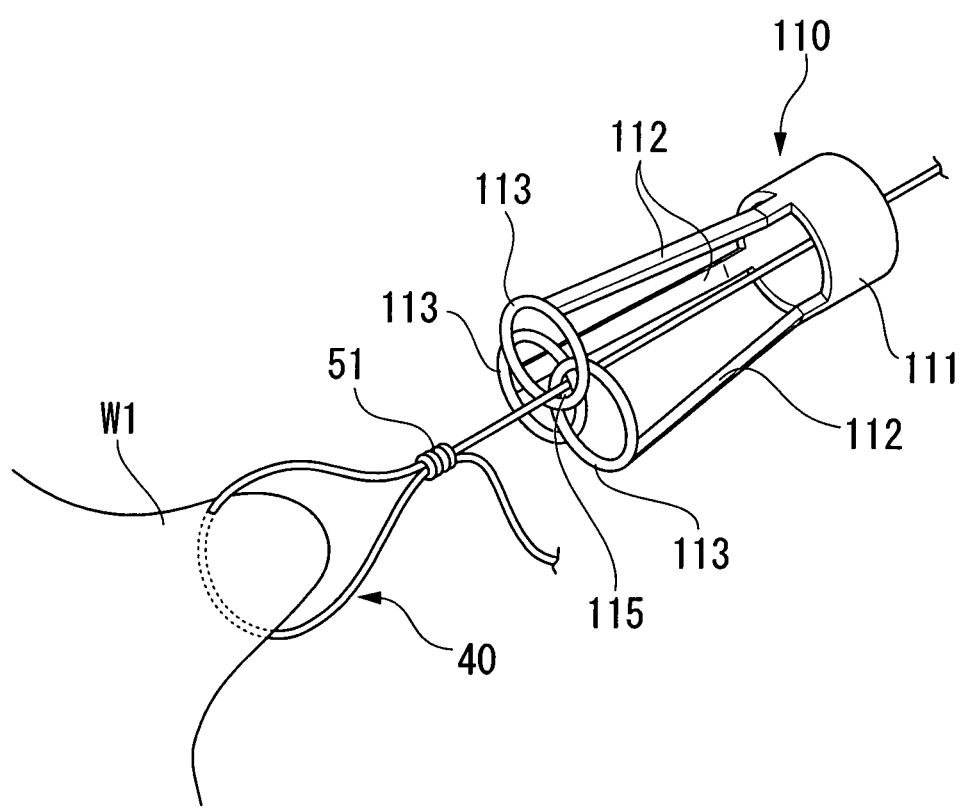
FIG. 30 is a diagram showing the knot forming loop being pressed by means of a space formed by a plurality of the rings.

Here, constitution of the knot pusher 59 is not limited to that shown in FIG. 25, but any of the foregoing embodiments may be employed. A cutter 101 may also be provided such as a knot pusher 100 shown in FIG. 26 to FIG. 28. The knot pusher 100 has a body 103 of tubular shape which is attached to the distal end of the arm sheath 19 via an O-ring 102 or the like. Inner circumference 103a of the body 103 functions as a loop delivery member which is capable of pushing out the knot forming loop 51. Inner diameter of the distal end of the body 103 is made larger so as to be able to recover the knot forming loop 51. Two V grooves 104, 105 opposing with each other by 180 degrees are formed on the outer circumference of the distal end of the body 103. The V grooves 104, 105 are formed in a size large enough to be able to pull in the ligature 40, and one of the V grooves 104 is formed as a cutter 101 provided with a thread cutting blade. The other V groove 105 does not have the thread cutting blade. To tighten the ligature 40, the knot pusher 100 is moved forward thereby pushing out the knot forming loop 51. Then as shown in FIG. 27, a portion of the ligature 40 on the proximal end side than the knot forming loop 51 is pulled into the V groove 105 without thread cutting blade, and the knot pusher 100 is moved further forward. This makes the V groove 105 function as the loop delivery portion so as to move the knot forming loop 51 toward the tissue W1; thereby the tissue W1 is ligated. Then as shown in FIG. 28, the ligature 40 is pulled into the V groove 104 with the thread cutting blade (the cutter 101) and cut off. The knot pusher 100 makes it possible to cut off the ligature 40 without preparing a separate tool for cutting off the ligature 40. A knot pusher 110 as shown in FIG. 29, where three pusher arms 112 are extend from a base portion 111 and rings 113 are provided at the distal end of each of the pusher arms, may also be employed. The thread receiving cartridge 91 is inserted in such a state that the rings 113 overlap with each other. The ring 113 has inner diameter which is substantially equal to the outer diameter of the loop holding portion 93 and is disposed on the proximal end side than the knot forming loop 51. When the knot pusher 110 is moved forward in order to ligate a tissue, the rings 113 located at the distal end functions as the loop delivery members so as to push the knot forming loop 51 out of the loop holding portion 93. As the rings 113 move beyond the loop holding portion 93, the assembly expands in such a configuration that the rings partially overlap with each other as shown in FIG. 30, and the ligature 40 is passed through a space 115 formed at the center. As the knot pusher 110 is moved forward further, the ring 113 which forms the circumference of the space 115 functions as the knot delivery portion so that the knot forming loop 51 is pressed into the tissue W1. The knot pusher 110 as described above functions such that as the rings 113, functions as the loop delivery portion, are passed through the loop holding portion 93, the loop delivery portion is prevented from coming off the loop holding portion 93. Also because the plurality of rings 113 are formed so as to form a space 115 in the natural state, when the ligature 40 is passed through the space 115 formed at the center of the plurality of rings 113, the knot can be surely pressed as the ligature 40 does not come off the knot pusher 110.

Figure 32:
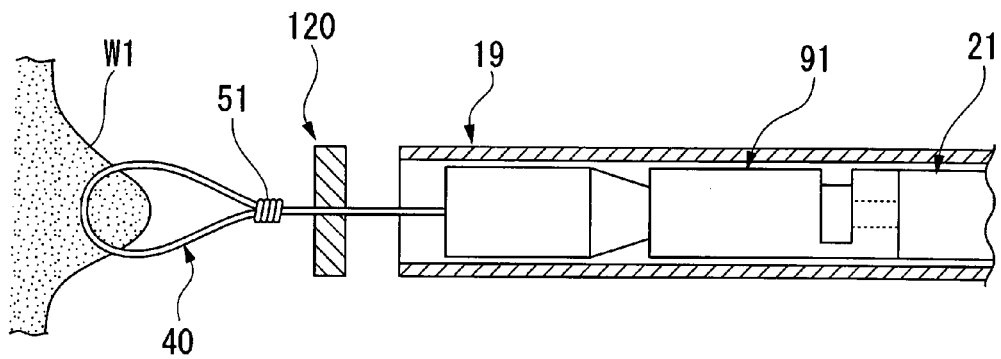
FIG. 32 is a diagram showing the knot pusher being pushed out of the thread receiving portion.
Figure 33:
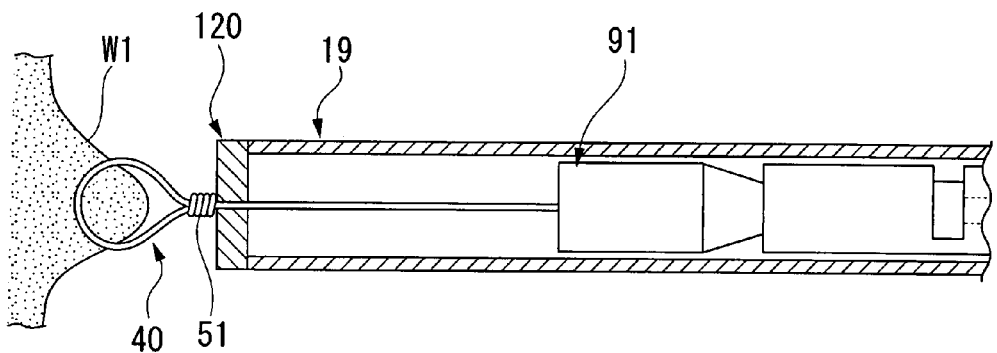
FIG. 33 is a diagram showing the knot pusher being pushed by the arm sheath to move the knot forming loop toward the tissue.

Fourth embodiment of the present invention will now be described with reference to FIG. 31 to FIG. 33. This embodiment differs from the third embodiment in that the knot pusher is constituted detachably. Accordingly, constituent components identical with those of the third embodiment are denoted with the same reference numerals, and identical descriptions will be omitted. While the embodiment below describes the thread receiving portion as a form of a detachable cartridge, the thread receiving portion may also be fixed on the inner sheath.

Figure 31:
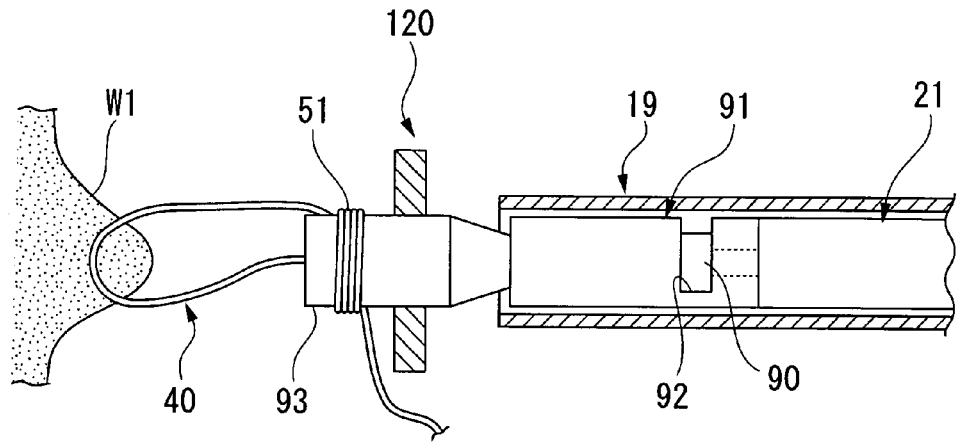
FIG. 31 is a diagram showing the knot pusher formed of an elastic material mounted on the thread receiving portion.

As shown in FIG. 31, the knot pusher 120 is made of an elastic material which is formed in an annular shape and is mounted around the outer circumference of the thread receiving cartridge 91. The knot pusher 120 is mounted at a position on the distal end side than the knot forming loop 51 and used. The knot pusher 120 is formed such that, when the knot pusher 120 is removed from the thread receiving cartridge 91, the inner diameter of the knot pusher 120 becomes smaller than the outer diameter of the knot forming loop 51, and the outer diameter of the knot pusher 120 becomes larger than the outer diameter of the arm sheath 19.

To make a ligating operation in this embodiment, the thread receiving cartridge 91 around which the knot pusher 120 is mounted is mounted on the inner sheath 21. The pair of clamping members 36, 42 are opened and closed so as to pass the ligature 40 through the tissue W1 and the distal end needle portion 38 of the curved needle 37 is recovered in the thread receiving cartridge 91. To tighten the ligature 40, the second handle 12 is moved forward so as to move the arm sheath 19 forward. As the distal end of the arm sheath 19 pushes the knot pusher 120, the knot pusher 120 pushes the knot forming loop 51 out of the loop holding portion 93. As shown in FIG. 32, the knot pusher 120 which is pushed out of the loop holding portion 93 shrinks in a radial direction so that the inner diameter thereof becomes smaller than the knot forming loop 51. When the knot pusher 120 is pushed further by the arm sheath 19 as shown in FIG. 33, the knot pusher 120 presses the knot forming loop 51 onto the tissue W1. Then the knot forming loop 51 is tightened to form a knot, so that the tissue W1 is ligated by the ligature 40. Ligation of the tissue W1 is completed by cutting off the ligature 40 with scissors or the like not shown in the drawing. The knot pusher 120 may be either taken out of the human body or left in the human body.

According to this embodiment, since the knot pusher 120 is made of the elastic material, the ligature 40 does not come off the knot pusher 120, and the tissue W1 can be reliably tied up with the ligature 40. Since constitution of the knot pusher 120 can be simplified, cleaning can be carried out easier at lower cost.

Fifth embodiment of the present invention will now be described with reference to FIG. 34 to FIG. 39. This embodiment relates to a ligating apparatus which ligates mainly blood vessels. The object to be ligated is not limited to blood vessels, but it may be a small tubular tissue. Constituent components identical to those of the foregoing embodiments are denoted with the same reference numerals, and identical descriptions will be omitted.

Figure 34:
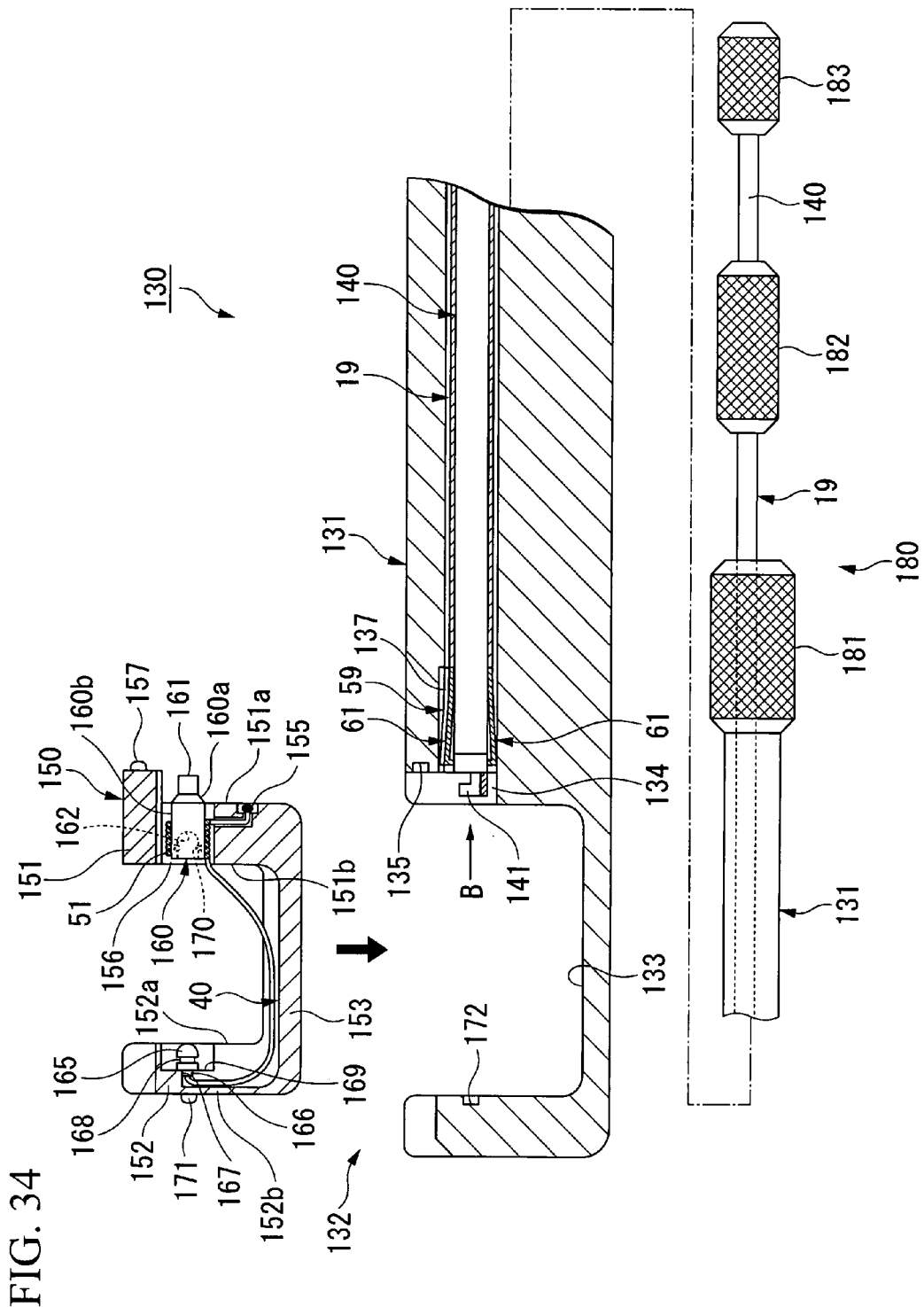
Figure 35:
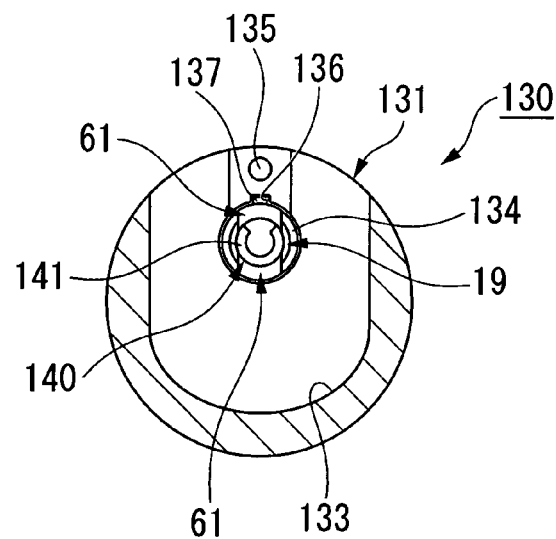
FIG. 35 is a sectional view in the direction of arrow B of FIG. 34.

As shown in FIG. 34, the ligating apparatus 130 is provided with a manipulating portion 132 formed at the distal end of a shaft 131 which is made of a hard material and constitutes the inserting part body. The shaft 131 has a notch formed in a concave shape at the distal end thereof, and a through hole 134 is formed so as to open in the notch 133. As shown in FIG. 34 and FIG. 35, an opening at the distal end of the through hole 134 is partially cut off to form a concave portion 135. Moreover, a key slot 136 is formed inside of the through hole 134.

The arm sheath 19 is movably provided back and forth through out the through hole 134. A key 137 is fit in the key slot 136 on the outer circumference of the distal end of the arm sheath 19. A pair of pusher arms 61 of the knot pusher 59 is further secured at the distal end of the arm sheath 19. The pusher arms 61 may have any one of the forms of the foregoing embodiments. A holding member rod 140 is movably provided back and forth through out the arm sheath 19. A joint portion 141 is provided at the distal end of the holding member rod 140. The joint member 141 partially opens, and is so positioned by the key slot 136 and the key 137 that the opened portion directs in the direction of the cutoff portion of the through hole 134 (open end of the notch 133 of the shaft 131).

A cartridge 150 which, together with the shaft 131, forms the manipulating portion 132 is mounted in the notch 133 of the shaft 131. The cartridge 150 has such a concave shape as a pair of walls 151, 152 which are separated from each other are connected by an intermediate portion 153, with such an external shape that can be inserted in the notch 133 of the shaft 131. A proximal end side of the ligature fixing portion 155, an opening of a through hole 156, and a projection 157 are formed on the external surface 151a of the wall 151 in this order from the side of the intermediate portion 153. The projection 157 is formed on a protruding portion protruding from the external surface 151a, and is capable of engaging with the concave portion 135 on the side of the shaft 131. The through hole 156 is formed at a position communicating with the through hole 134 on the side of the shaft 131, so as to extend from the external surface 151a to the inner surface 151b of the wall 151. A thread receiving portion 160 is accommodated in the through hole 156. The proximal end 161 of the thread receiving portion 160 is constituted so as to be capable of engaging with the joint portion 141 the side of the shaft 131. A loop holding portion 160b, on the circumference of which the knot forming loop 51 of the ligature 40 is placed, which is flared out by a tapered portion 160a is provided on the distal side than the proximal end 161. An insertion hole 162 opens at distal end surface of the loop holding portion 160b. The second end of the ligature 40 that forms the knot forming loop 51 passes through the wall portion 151 and is fixed at the proximal end side of the ligature fixing portion 155.

The ligature 40 on the first end side than the knot forming loop 51 is routed substantially along the concaved inner surface of the cartridge 150, and the first end is drawn into the proximal end 166 of the distal end member 165 and is fastened therein. The distal end member 165 is accommodated in a concave portion 169 formed in the inner surface 152a of the wall 152 so as not to be exposed when viewed sideways. The distal end member 165 is located at a position which faces the through hole 156 of the opposing wall 151 facing the through hole 156. The proximal end 166 of the distal end member 165 is fitted in a groove 167 formed in the wall portion 152, and the distal end of the distal end member 165 which flares out from the proximal end 166 is formed in a spherical shape. An annular groove 168 is formed on the proximal end side than the spherical portion. The distal end member 165 has such a size that can be inserted into the insertion hole 162 of the thread receiving portion 160, so that the groove 168 of the distal end member 165 engages with the spring 170 provided inside of the insertion hole 162. A projection 171 is formed on the external surface 152b of the wall portion 152.

A control portion 180 is provided at the proximal end of the shaft 131. The control portion 180 includes a shaft handle 181 secured onto the shaft 131, an arm sheath handle 182 secured onto the arm sheath 19 which is drawn out of the shaft 131, and a rod handle 183 secured onto the holding member rod 140 which is drawn out of the arm sheath 19.

Operation according to this embodiment will be described below. Before starting the procedure, the cartridge 150 is mounted on the shaft 131. The projection 171 formed on the external surface 152b of the wall portion 152 of the cartridge 150 engages with the concave portion 172 of the shaft 131. On the side of the wall portion 151 of the cartridge 150, the projection 157 engages with the concave portion 135 and the proximal end portion 161 of the thread receiving portion 160 engages with the joint portion 141. Thus the cartridge 150 is mounted on the shaft 131 and, at the same time, the thread receiving portion 160 becomes possible to be moved back and forth by means of the rod handle 183.

Figure 36:
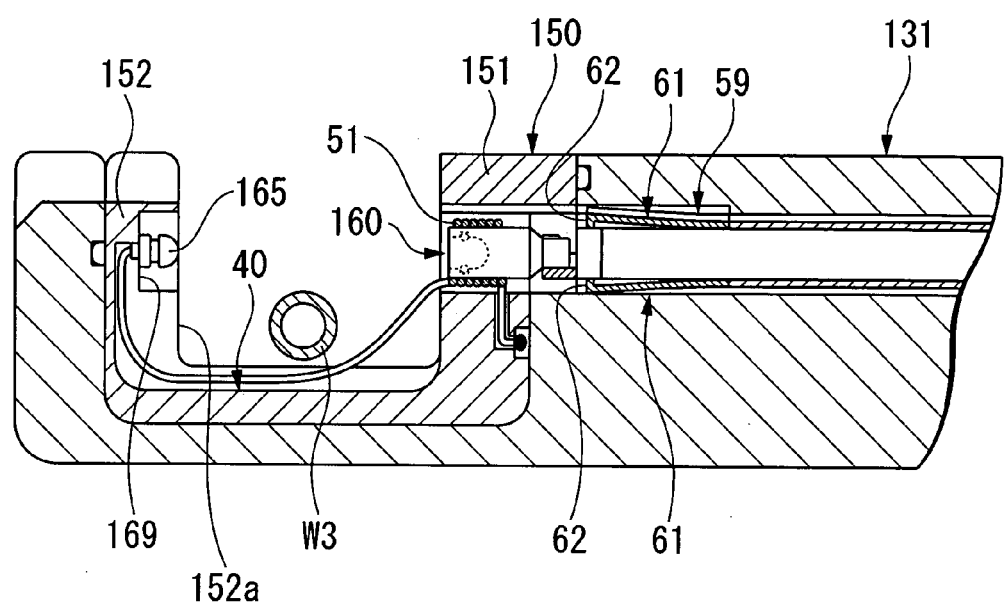
FIG. 36 is a diagram showing the state of the cartridge being mounted.
Figure 37:
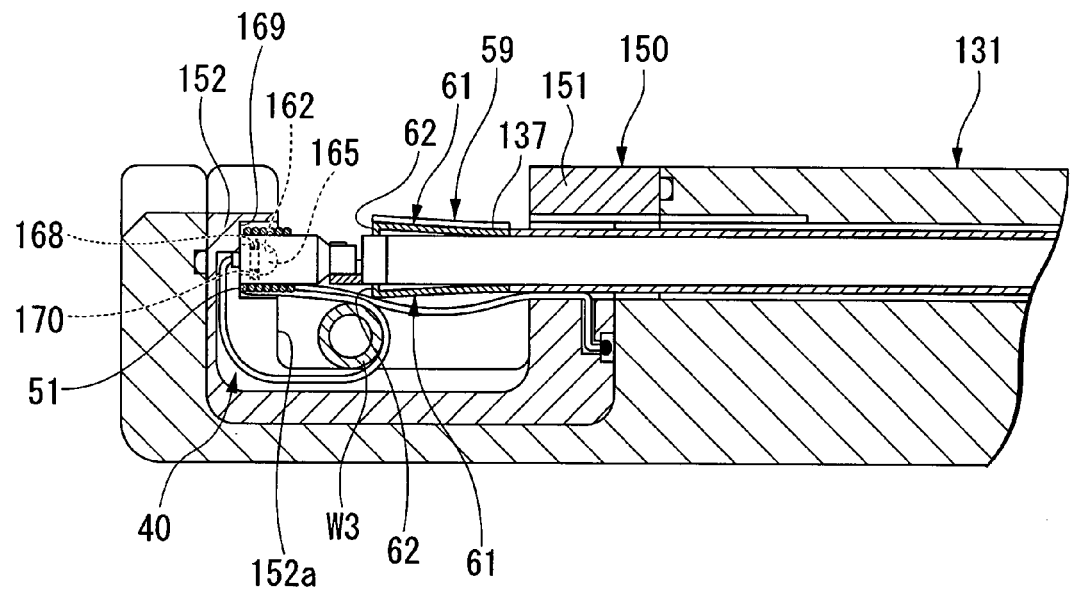
FIG. 37 is a diagram showing the state of the holding member moved forward to lock the distal end member.
Figure 38:
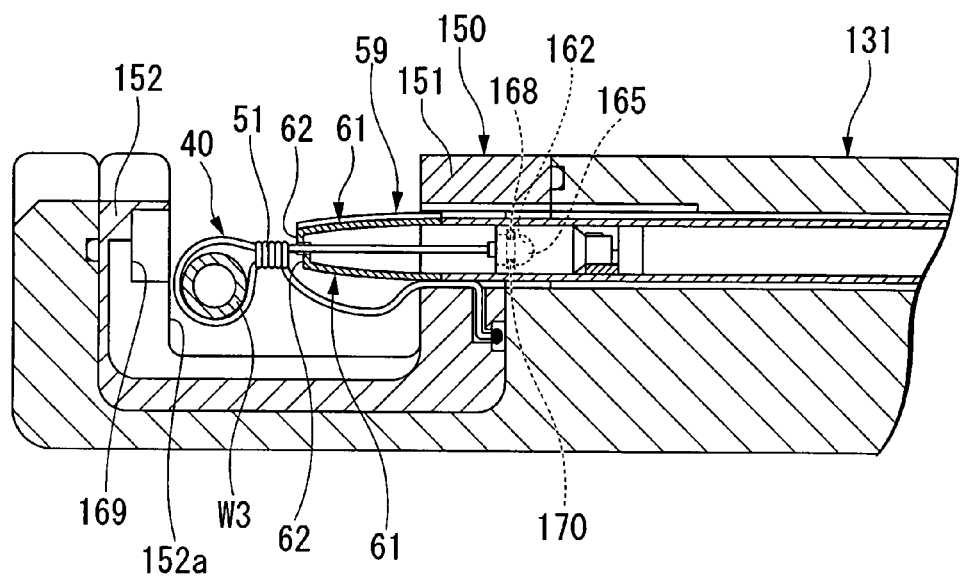
FIG. 38 is a diagram showing the state of blood vessel being ligated.

To perform the procedure, a blood vessel W3 is inserted on the concaved inner surface of the cartridge 150 as shown in FIG. 36, so that the ligature 40 routed along the cartridge 150 passes around the blood vessel W3. When the arm sheath handle 182 (refer to FIG. 34) is moved forward, the thread receiving portion 160 and the knot pusher 59 are pushed out of the wall portion 151 of the cartridge 150 toward the opposing wall portion 152. As shown in FIG. 37, then the distal end member 165 is recovered in the insertion hole 162. The groove 168 of the distal end member 165 engages with the spring 170. When the arm sheath handle 182 is moved backward, the distal end member 165 which is engaged with the thread receiving portion 160 is pulled out of the wall portion 152. At this time, the first end of the ligature 40 is fastened onto the thread receiving portion 160, from which the ligature stretches to form a large loop that encloses the blood vessel W3 and returns to the thread receiving portion 160 and then reaches the proximal end side of the ligature fixing portion 155 by passing through the knot forming loop 51 of the loop holding portion 160b.

The arm sheath handle 182 is stopped when the knot pusher 59 is reached near the blood vessel W3, and then only the rod handle 183 (refer to FIG. 34) is moved backward. Then the thread receiving portion 160, together with the holding member rod 140, is pulled into the arm sheath 19. The knot pusher 59 is expanded by the tapered portion 160a of the retracting thread receiving portion 160, so as to push the knot forming loop 51 out of the thread receiving portion 160, while making contact with the outer circumference of the thread receiving portion 160 (loop holding portion 160b).

When the thread receiving portion 160 moves further to the proximal end side than the knot pusher 59, the delivery portion 62 of the knot pusher 59 closes to hold the knot forming loop 51. While the ligature 40 is drawn as the thread receiving portion 160 moves backward, the knot forming loop 51 is in contact with the delivery portion 62 of the knot pusher 59 and does not move. Similarly, the proximal end of the ligature 40 which is fastened onto the cartridge 150 does not move either. As a result, position of the blood vessel W3 does not move while the loop 51 moves along the ligature 40. Accordingly, the loop of the ligature 40 enclosing the blood vessel W3 is pulled up so that the knot forming loop 51 forms a knot and constricts the blood vessel W3. Ligation of the blood vessel W3 is completed as the extra ligature 40 is cut off by means of scissors or the like not shown in the drawing.

According to this embodiment, since the knot pusher 59 is used to push the knot forming loop 51 that forms the knot out of the thread receiving portion 160, tension is not applied to the ligature 40 placed around the blood vessel W3 when the knot forming loop 51 is pushed out. This reduces the load applied to the blood vessel W3. Moreover, during the process of ligating the blood vessel W3 too, the load applied to the blood vessel W3 can be reduced since the ligature 40 is tightened with the knot forming loop 51 that is held by the knot pusher 59 as the starting point.

Also because the thread receiving portion 160 and the ligature 40 are placed on the cartridge 150 which is attached on and detached from the shaft 131, the operation of setting the ligature 40 becomes easier during the preparation for the procedure. Moreover, since consecutive operations of ligation can be carried out simply by replacing the cartridge 150, the procedure can be done in a shorter period of time. Also since the constitution of the side of the shaft 131 is made simple, cleaning is made easier.

Figure 39:
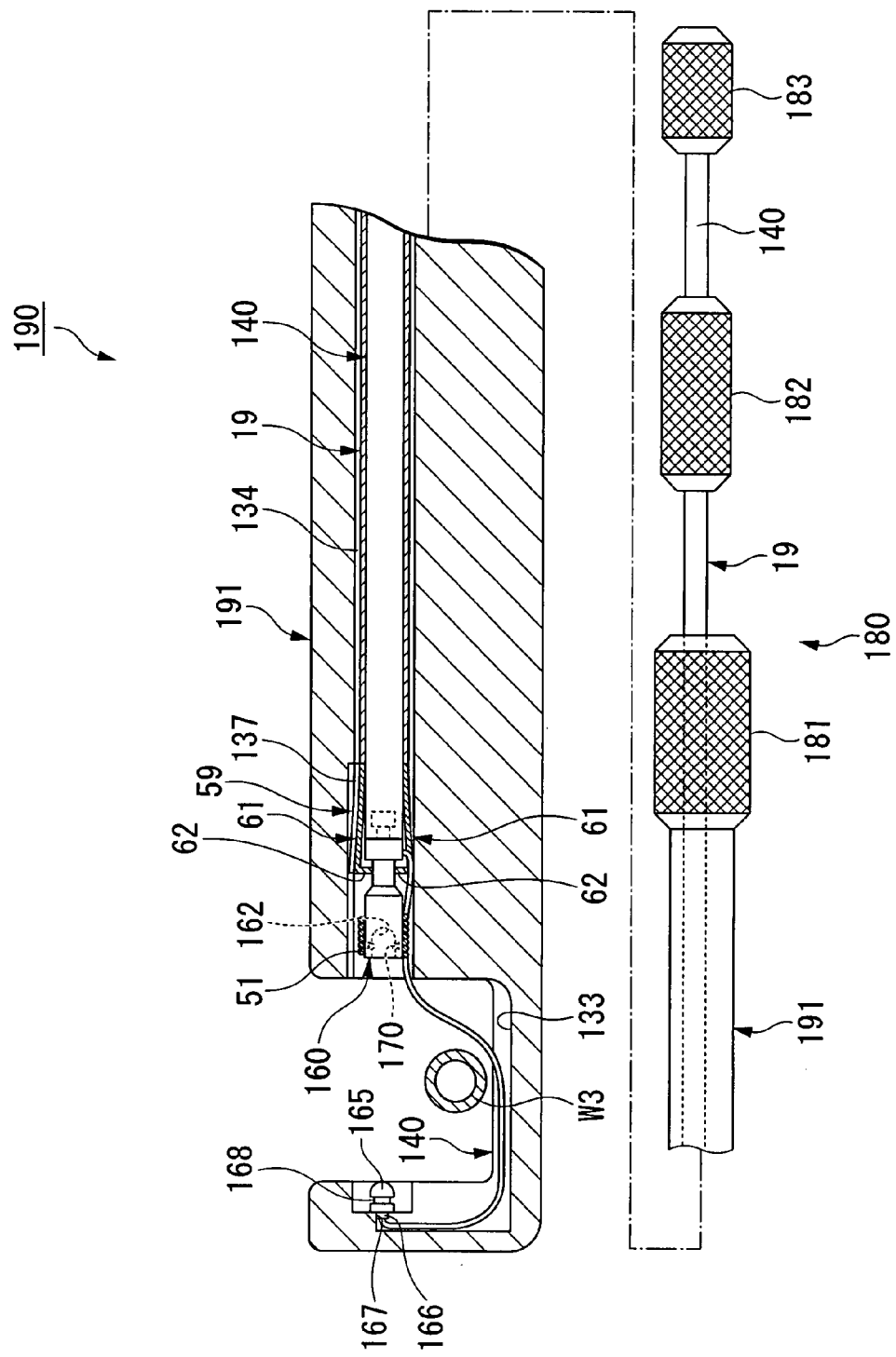
FIG. 39 is a diagram showing a constitution where the holding member and the distal end member are disposed in the shaft.

A variant of this embodiment is shown in FIG. 39. This ligating apparatus 190 is not provided with a detachable cartridge but the thread receiving portion 160 and the distal end member 165 are disposed to oppose each other around the periphery of a concaved notch 133 formed at the distal end portion of a shaft 191. To ligate the blood vessel W3, the arm sheath handle 182 is moved forward so as to recover the distal end member 165 in the thread receiving portion 160. When the arm sheath handle 182 is retracted until the knot pusher 59 comes near the blood vessel W3, only the rod handle 183 is moved backward so as to drop the knot forming loop 51 from the thread receiving portion 160 with the knot pusher 59. As the rod handle 183 is pulled further, the ligature 40 can be pulled up while holding the knot forming loop 51 by means of the knot pusher 59, the distal end of which has closed, thereby it is possible to ligate the blood vessel W3 with the knot forming loop 51 as the starting point. The ligating apparatus 190 achieves effects similar to those described previously, except for the effects unique to the cartridge. Moreover, since the key slots or the like used to attach or detach the cartridge are not necessary, the apparatus can be made in simpler constitution.

The present invention is not limited to the embodiments described above, and can be used in wider applications.

Figure 40:
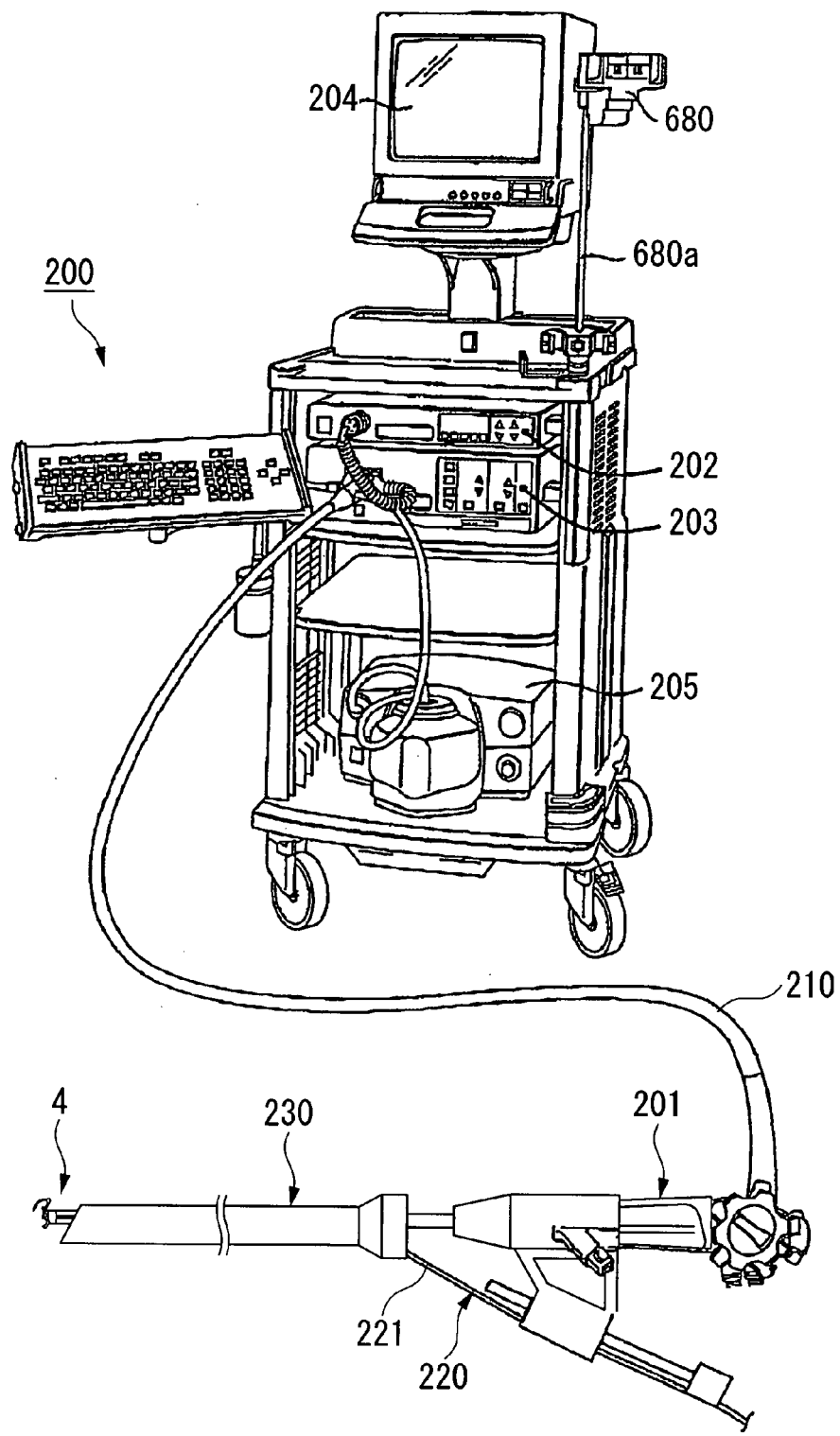
FIG. 40 is a diagram explaining a case where the ligating apparatus and the soft endoscope are used together.

For example, the embodiments described above relate to cases where the ligating apparatus is used in combination with a laparoscope, but the ligating apparatus can also be used, for example, with a flexible endoscope system 200 as shown in FIG. 40. The endoscope system 200 includes an endoscope 201, an image processor 202, a light source 203, a monitor 204 for observation, and a suction device 205. Light flux emitted from the light source apparatus 203 is guided through a universal cable 210 to the distal end of the endoscope 201, so as to illuminate inside of the human body. An image taken with an imaging device provided at the distal end of the endoscope 201 is sent to the image processing apparatus 202 and is displayed on the monitor 204. The endoscope 201 has an operation channel through which treatment instruments such as forceps are passed.

A ligating apparatus 220 used together with the endoscope system 200 as described above has a constitution similar to that of one of the embodiments described above, except that a flexible insertion portion 221 is provided. The endoscope 201 and flexible insertion portion 221 of the ligating apparatus 220 are inserted into a human body by passing through a flexible overtube 230.

In this embodiment of a ligating apparatus, when constricting the part of the organ to be ligated with the ligature by passing the first end of the ligature through the inside of the knot forming loop, the part of the organ to be ligated is not pulled by pulling up the ligature but the knot forming loop is moved to the part of the organ to be ligated by means of the knot delivery member of the knot pusher.

In a ligating apparatus of another embodiment, since the knot forming loop of the ligature is pushed out of the loop holding portion by the loop delivery portion, the part of the organ to be ligated is not loaded when pushing out the knot forming loop.

In a ligating apparatus of another embodiment, when a part of the organ to be ligated is ligated, the extra ligature is cut off by the thread cutting blade of the knot pusher.

In a ligating apparatus of another embodiment, when the knot forming loop is pushed toward the part of the organ to be ligated so as to form a knot, the knot delivery portion is surely closed by means of the opening preventing member so that the knot delivery portion does not accidentally open to allow the ligature to come off the knot pusher.

In a ligating apparatus of another embodiment, once the ligature is passed through the guide groove, the ligature does not come off the knot pusher when the knot forming loop is pushed out by the loop delivery portion.

In a ligating apparatus of another embodiment, when the ligature is passed through the space formed by the rings, the ligature does not come off the knot pusher when the knot forming loop is pushed out by the loop delivery portion. Since the rings are biased to move apart from each other, the knot pusher can be put in standby with the first fastening portion receptor portion being kept in the state of passing through the rings.

According to the present invention, when the first end of the ligature is passed through a loop of the ligature that forms a knot and is tightened, load applied to the organ to be ligated can be reduced since the knot delivery portion which pushes the loop toward the organ to be ligated and forms the knot is provided so that the organ to be ligated can be ligated without pulling it up.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description but is only limited by the scope of the appended claims.

What is claimed is:

1. A ligating apparatus that ligates tissue with a ligature, the ligating apparatus comprising:
    an inserting part body;
    a needle portion which is disposed at a distal end portion of the inserting part body, wherein the needle portion is fastened to a first end of a ligature, has a pointed top, and is configured to move so as to penetrate a tissue;
    a thread receiving portion which is disposed at the distal end portion of the inserting part body, wherein the thread receiving portion includes a tubular member having an internal space in which the needle portion is capable of being inserted, a fastening portion to which the needle portion is fastened in a longitudinal direction of the tubular member when the needle portion is inserted in the internal space, and a loop holding portion holding a loop which is formed by winding the ligature around an outer circumference of the tubular member;
    a knot pusher having a pair of knot delivery portions which is provided so as to freely move in the longitudinal direction of the tubular member relative to the loop wound around the outer circumference of the tubular member, wherein the pair of knot delivery portions pinch an outer circumference of the thread receiving portion, come into contact with the loop, and push the loop forward, when moved in the longitudinal direction;
    a pair of thread cutting blades, wherein one of the pair of thread cutting blades formed in an end of one of the pair of knot delivery portions faces the other of the pair of thread cutting blades formed in an end of the other of the pair of knot delivery portions; and
    a cover sheath configured to advance and retract relative to the knot pusher, wherein the knot pusher is inserted into the cover sheath,
    wherein
    the pair of knot delivery portions has a restoring force acting on itself such that the pair of knot delivery portions approach each other and reach a restored state when the pair of knot delivery portions move forward beyond a distal end of the thread receiving portion;
    notches formed on the pair of knot delivery portions such that the ligature extending from the needle portion inserted in the internal space is capable of being inserted into a gap between the pair of thread cutting blades when the pair of knot delivery portions reaches the restored state,
    wherein the loop is configured to be detached from the outer circumference of the tubular member by the pair of knot delivery portions pushing the loop forward,
    wherein the pair of knot delivery portions is configured to come into contact with the loop detached from the outer circumference of the tubular member, and move the loop to a target organ to be ligated with the ligature extending in the notches and from the needle portion which is inserted in the internal space, and
    wherein the pair of knot delivery portions is configured to cut the ligature extending from the needle portion inserted in the internal space by the pair of thread cutting blades approaching each other by an inner surface of the cover sheath pushing the pair of knot delivery portions when the cover sheath advances relative to the pair of knot delivery portions.

2. The ligating apparatus according to claim 1, wherein the pair of knot delivery portions of the knot pusher is configured to open and close so as to pinch the ligature.

3. The ligating apparatus according to claim 1, wherein the pair of knot delivery portions is provided with a guide groove which guides the ligature.

4. The ligating apparatus according to claim 1, wherein the pair of knot delivery portions is a pair of pusher arms.

5. The ligating apparatus according to claim 1, wherein the restoring force is generated by releasing engagement between the pair of knot delivery portions and the outer circumference of the thread receiving portion.

6. The ligating apparatus according to claim 1, further comprising a second fastening portion which is disposed at the distal end portion of the inserting part body and is fastened to a second end of the ligature located opposite to the first end of the ligature.

* * * * *